United States Patent
Selby et al.

(10) Patent No.: US 10,422,783 B2
(45) Date of Patent: Sep. 24, 2019

(54) GREASE OXIDATION

(71) Applicants: Theodore W. Selby, Midland, MI (US); Jonathan C. Evans, Midland, MI (US); Gregory C. Miiller, Rhodes, MI (US); Calvin David Hugo, Munger, MI (US); Sarah R. Nuss-Warren, Midland, MI (US); Douglas J. Wirsing, Midland, MI (US)

(72) Inventors: Theodore W. Selby, Midland, MI (US); Jonathan C. Evans, Midland, MI (US); Gregory C. Miiller, Rhodes, MI (US); Calvin David Hugo, Munger, MI (US); Sarah R. Nuss-Warren, Midland, MI (US); Douglas J. Wirsing, Midland, MI (US)

(73) Assignee: TANNAS COMPANY, Midland, MI (US)

( * ) Notice: Subject to any disclaimer, the term of this patent is extended or adjusted under 35 U.S.C. 154(b) by 0 days.

(21) Appl. No.: 16/350,253

(22) Filed: Oct. 17, 2018

(65) Prior Publication Data
US 2019/0064137 A1 Feb. 28, 2019

Related U.S. Application Data

(62) Division of application No. 14/121,952, filed on Nov. 6, 2014.

(60) Provisional application No. 61/965,160, filed on Jan. 24, 2014, provisional application No. 61/962,464, filed on Nov. 7, 2013.

(51) Int. Cl.
*G01N 33/28* (2006.01)
*G01N 21/35* (2014.01)

(52) U.S. Cl.
CPC ......... *G01N 33/2888* (2013.01); *G01N 21/35* (2013.01); *G01N 33/2805* (2013.01); *G01N 2021/3595* (2013.01)

(58) Field of Classification Search
CPC ........... G01N 2021/3595; G01N 21/35; G01N 33/2805; G01N 33/2888
See application file for complete search history.

(56) References Cited

U.S. PATENT DOCUMENTS

| | | | |
|---|---|---|---|
| 7,678,328 B1* | 3/2010 | Secrist | B01J 19/0013 422/50 |
| 8,679,405 B1 | 3/2014 | Secrist et al. | |
| 2007/0032964 A1* | 2/2007 | Kaldor | G01N 33/2888 702/25 |
| 2017/0205355 A1 | 7/2017 | Selby et al. | |

OTHER PUBLICATIONS

T.W. Selby et al., "Grease Oxidation," U.S. Appl. No. 61/962,464, filed Nov. 7, 2013 A.D.
T.W. Selby et al., "Grease Oxidation," U.S. Appl. No. 61/965,160, filed Jan. 24, 2014 A.D.

(Continued)

*Primary Examiner* — Jennifer Wecker
(74) *Attorney, Agent, or Firm* — Christopher John Rudy

(57) ABSTRACT

Apparatus includes a pivotable, cradling framework that can hold a rotatable bomb instrument, which can include a hollow cylinder and a grease rack. This may be employed to effect a significantly improved version of the ASTM D942 Test Method. The same is useful in measurement of grease oxidation.

20 Claims, 19 Drawing Sheets

(56) References Cited

OTHER PUBLICATIONS

T.W. Selby et al., "A Comparative Study of Grease Oxidation Using an Advanced Bench Test Technique," Tech.Akad.Esslingen, Ostfildern, Germany, Jan. 21-23, 2014 A.D., 6 pages.

ASTM International Subcommittee D02.09.0E on Oxidation of Greases, ASTM D942-02 (Reapproved 2007)/IP Designation 142/85 (1982). 5 pages.

ASTM International Subcommittee D02.09.0C on Oxidation of Turbine Oils, ASTM D22727-09 (Reapproved 2011) 2009, pp. 846-864, "condensed," ASTM D2272-240, printed Feb. 27, 2018.

T.W. Selby et al., "Studies of the Oxidation Dynamics of Turbine Oils," ASTM Symp. on Ox'n & Testing of Turbine Oils, Norfolk, Va., Dec. 5, 2005, 17 pages.

G. Miiller, ASTM Subcommittee D02.09.0C on Oxidation of Turbine Oils, Research Report RR D02-1666, "Interlaboratory Study . . . for ASTM D2272-09 . . . ," Jun. 15, 2009, 16 pages.

T.W. Selby, "Modern Instrumental Method of Accurately and Directly Measuring the Useful Life of Turbine Oils," OilDoc Conference, Bavaria, Germany, Feb. 1-3, 2011, 32 pages.

O.Z. Pencheva et al., "Use of IR Spectroscopy in Research on Grease Oxidation," 1974 Cons. Bureau translation of Khim. Teckhn. Topliv i Masel, vol. 7, Jul. 1973, pp. 55-57.

Z.M. Zhang et al., "Infrared Refractive Index and Extinction Coefficient of Polyimide Films," Int'l J. Thermophys., vol. 19, No. 3, 1998, pp. 905-916.

S. Azad et al., Savant Laboratories, "An Advanced Technique for Grease Oxidation Measurement," NLGI 81st Annual Mtg., Palm Beach Gardens, Fla., Jun. 14-17, 2014, 15 pages.

S. Azad et al., Savant Laboratories, "Advanced Technique for Grease Oxidation Measurement," ca. Jun. 2014, 11 pages.

P.M. Cann et al., *Tribology Transactions*, vol. 50, Issue 2, 2007, "Grease Degradation in RoF Bearing Tests," Abstract, 2 pages.

Cann, P.M. et al., "Grease Degradation in R0f Bering Tests," Tribology Transactions, 50:187-197, 2007.

Hasegawa, K. et al., "Analysis of Aromatic Secondary Amines in Lubricating Oils," Bulletin of the Japan Petroleum Institute, vol. 5, Mar. 1963.

Pencheya, O.Z. et al., "Use of IR Spectroscopy in Research on Grease Oxidation," Chemistry and Technology of Fuels and Oils, vol. 9, Issue 7, pp. 561-563, Jul. 1973.

Bailey, W.W., et al., "Dynamic Oxidation Stability of Lubricating Greases," NGLI Spokesman, Apr. 1982, pp. 15-18.

Hurley, S., et al., "Infrared Characterisation of Grease Lubricant Films on Metal Surfaces," NGLI Spokesman, vol. 64, Oct. 2000, 18-pp. preprint paper No. 9924.

ASTM D4742-17, "condensed," printed Feb. 27, 2018.

ASTM D6022-06 (2012), "condensed," printed Feb. 27, 2018.

ASTM D6821-17, "condensed," printed Feb. 27, 2018.

\* cited by examiner

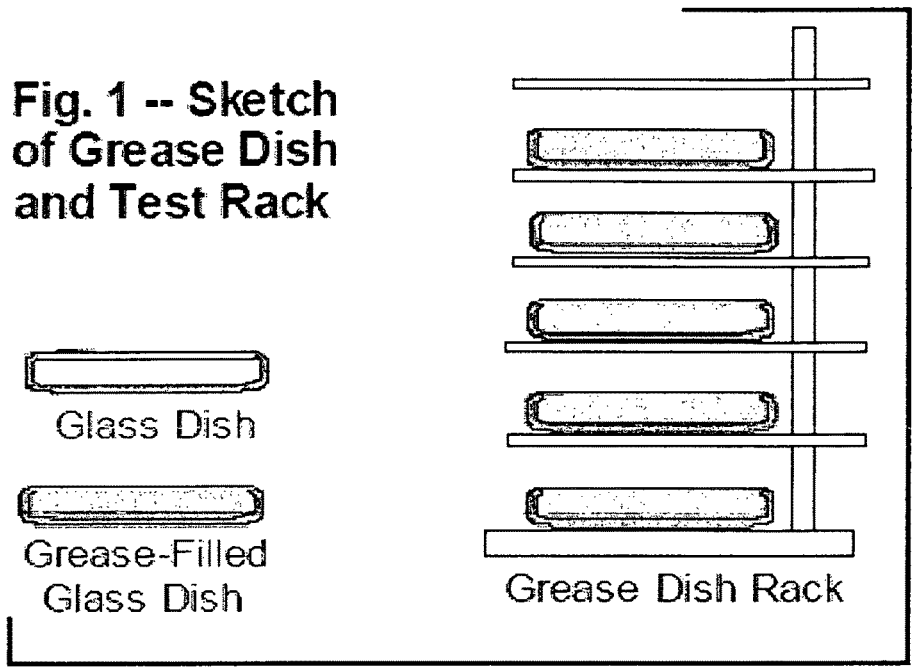
Fig. 1 -- Sketch of Grease Dish and Test Rack
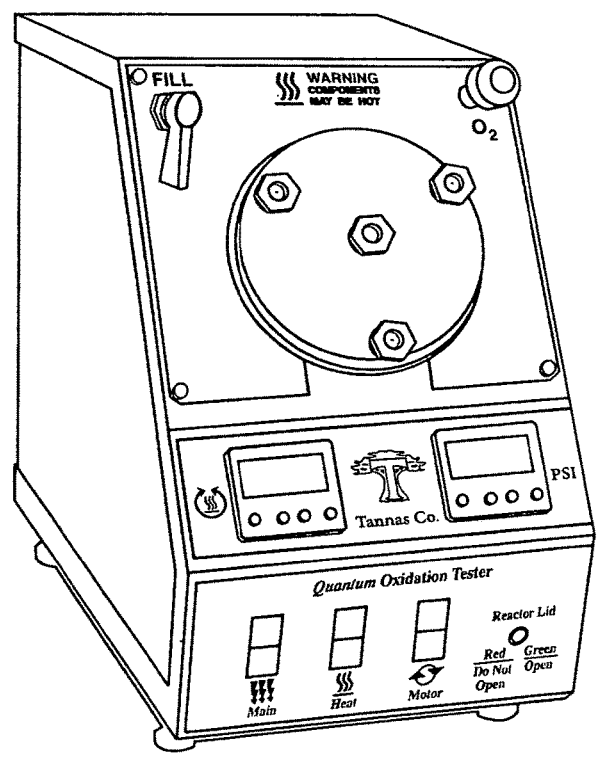
Fig. 2a

Fig. 4b
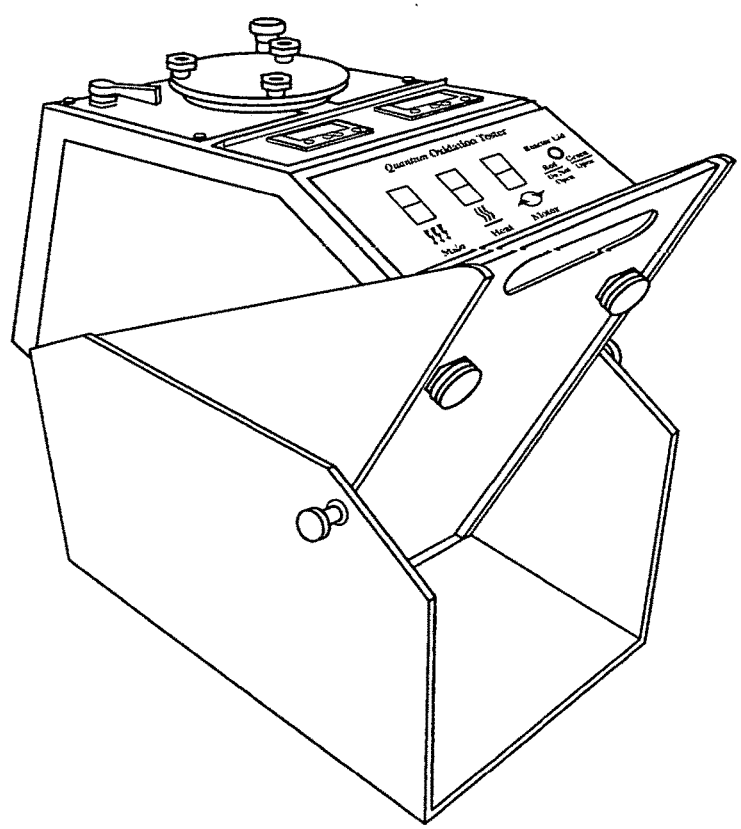
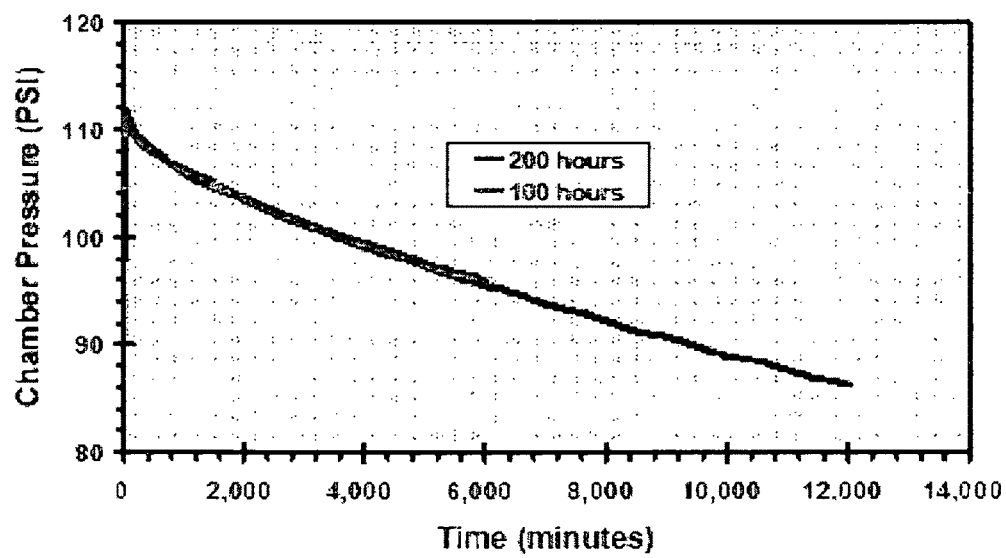

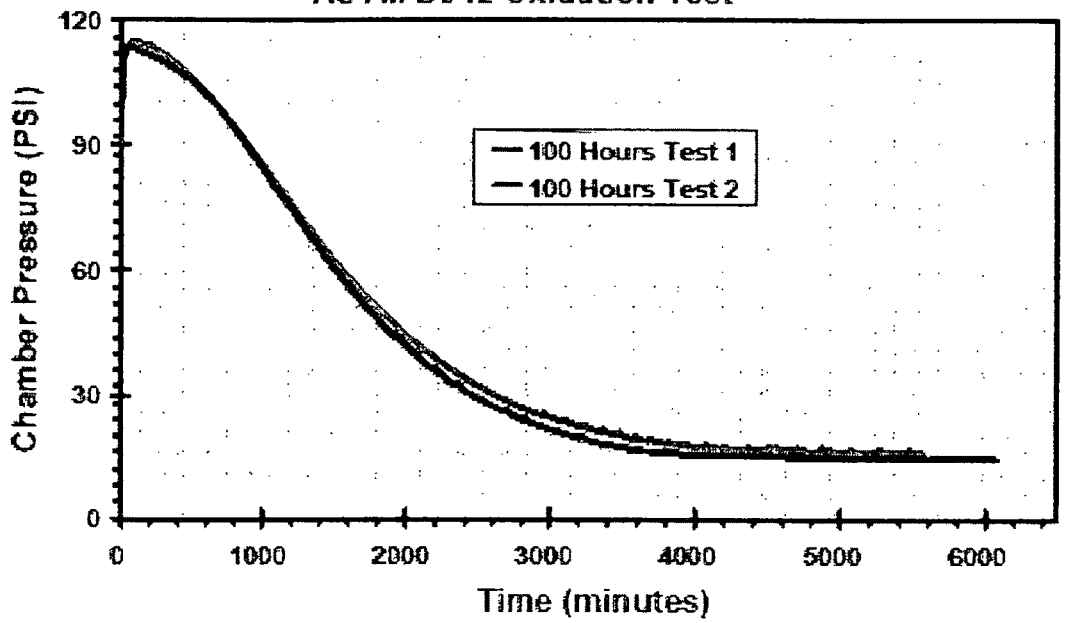
Fig. 6 – Response of Grease Sample #2 to ASTM D942 Oxidation Test
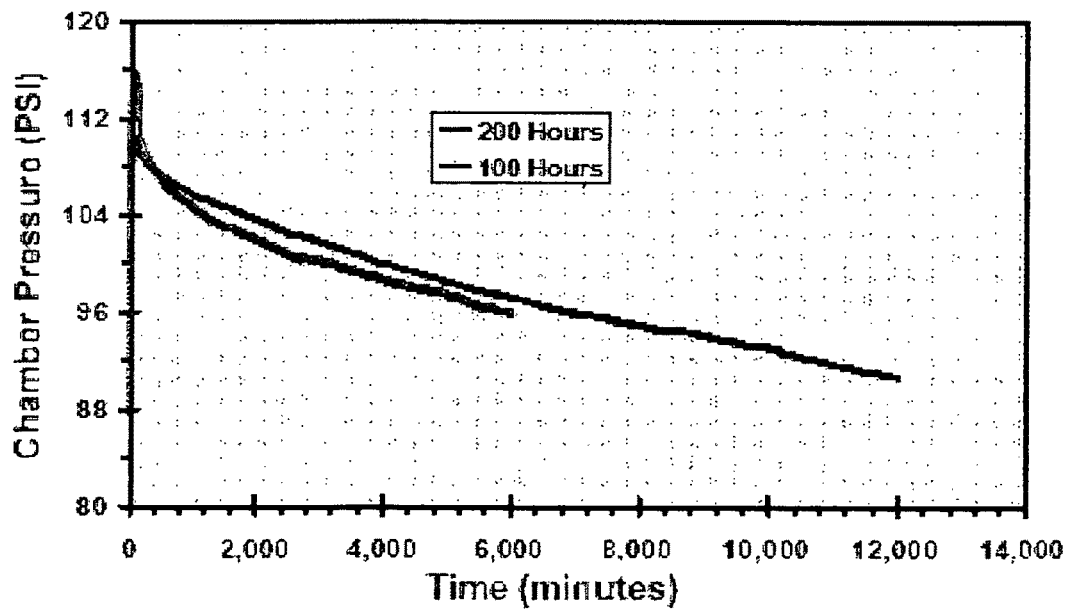
Fig. 7 – Effect of Oxidation on Grease #3 For 100 Hours and 200 Hours in ASTM D942

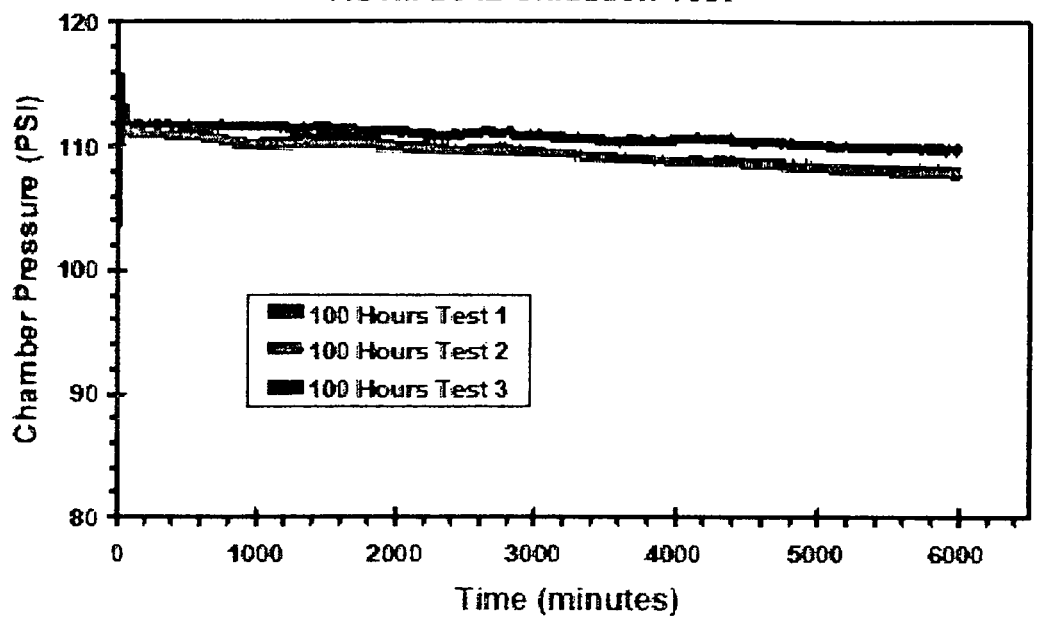
Fig. 8 – Response of Grease Sample #4 to ASTM D942 Oxidation Test
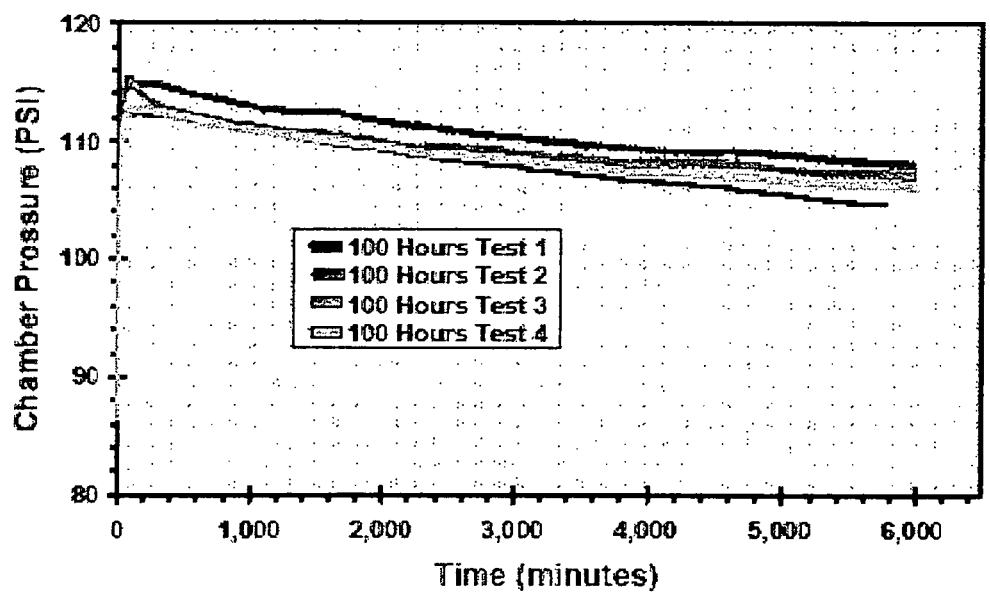
Fig. 9 – Response of Grease Sample #5 to ASTM D942 Oxidation Test

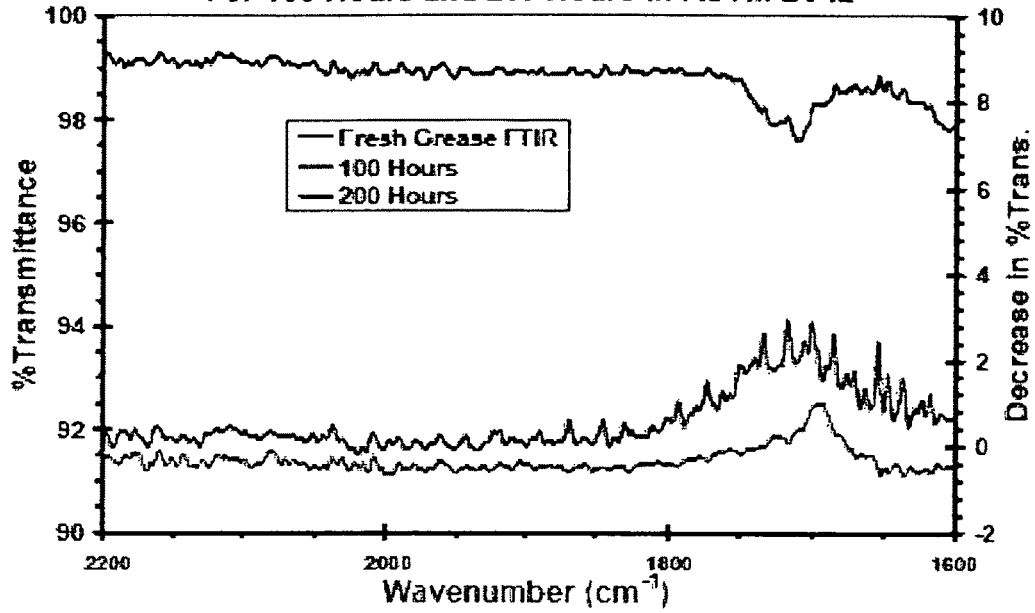
Fig. 10 – Effect of Oxidation on Grease #1 For 100 Hours and 200 Hours in ASTM D942
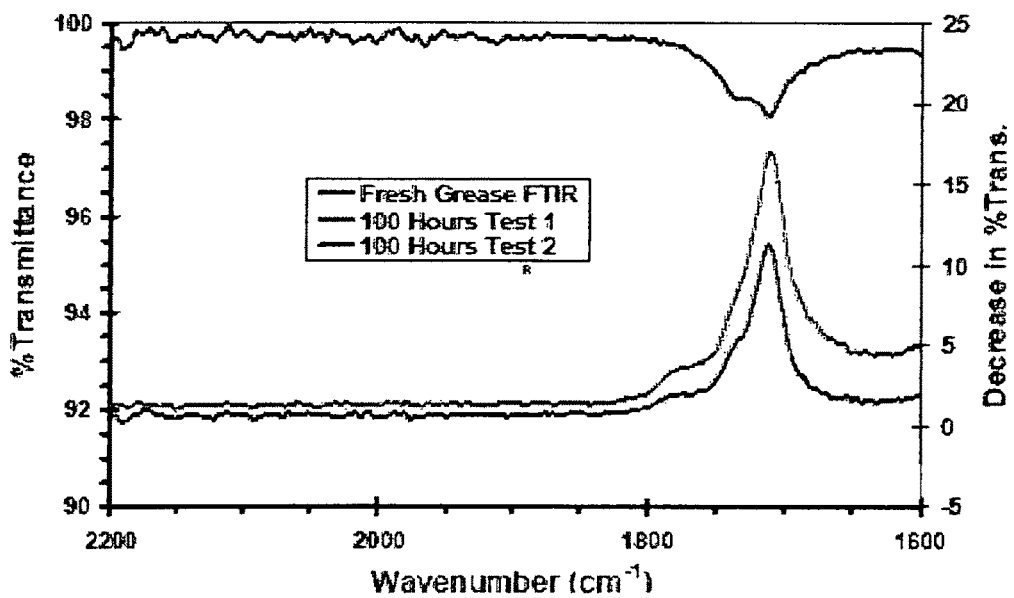
Fig. 11 – Effect of Oxidation on Grease #2 For 100 Hours in ASTM D942 Test

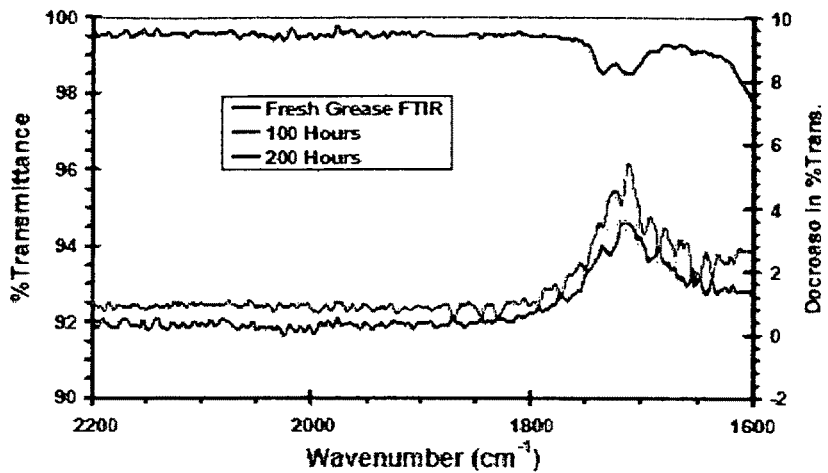
Fig. 12 – Effect of Oxidation on Grease #3 For 100 Hours and 200 Hours in ASTM D942
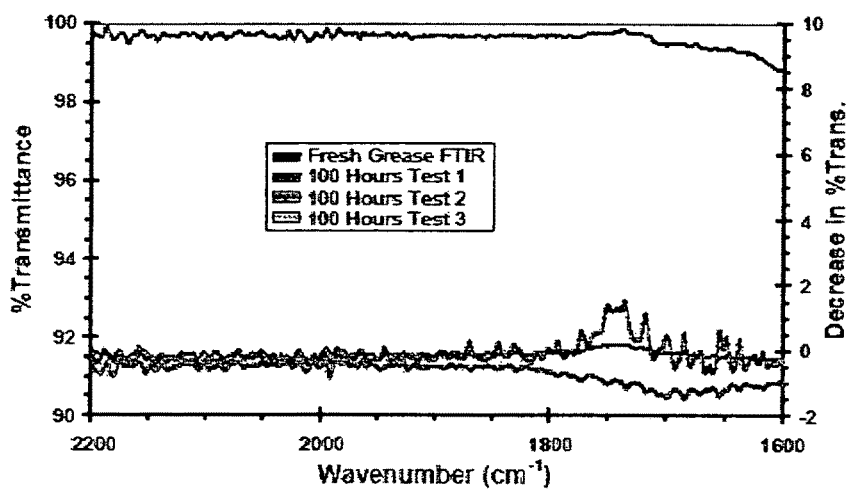
Fig. 13 – Effect of Oxidation on Grease #4 For 100 Hours in ASTM D942 Test
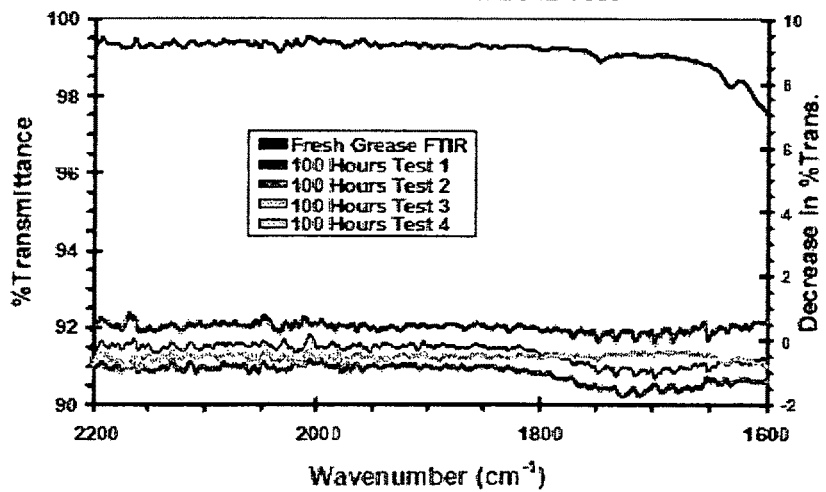
Fig. 14 – Effect of Oxidation on Grease #5 For 100 Hours in ASTM D942 Test

NOTES:
1) BREAK AND DEBURR ALL EDGES

Fig. 22
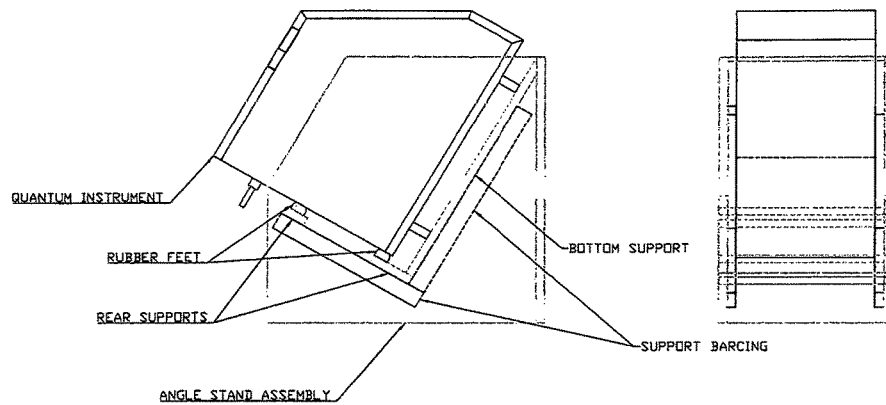
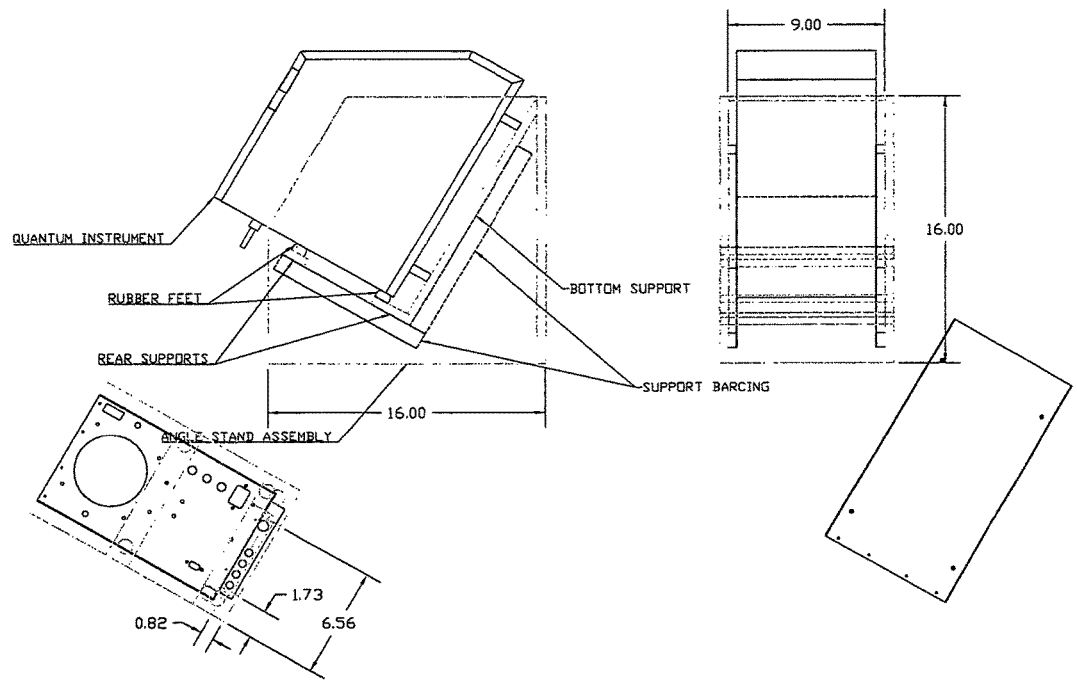

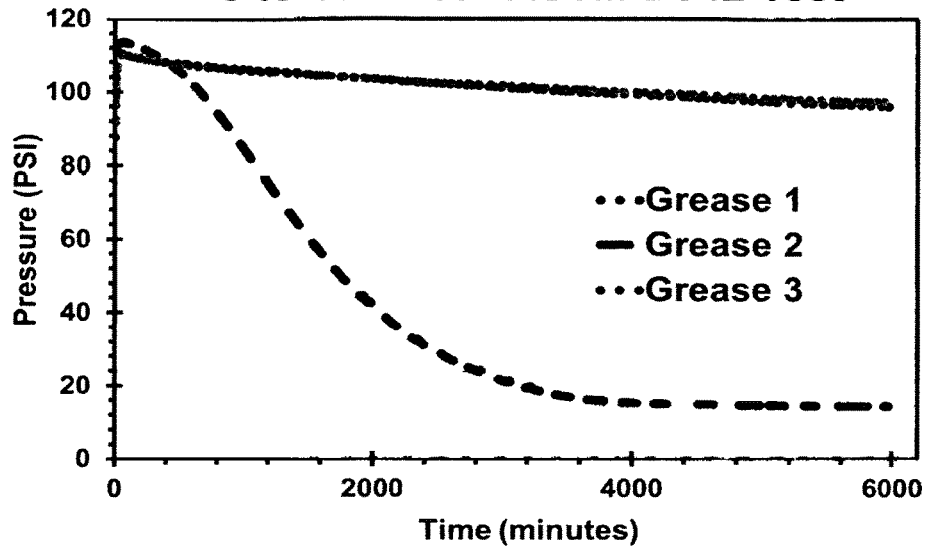
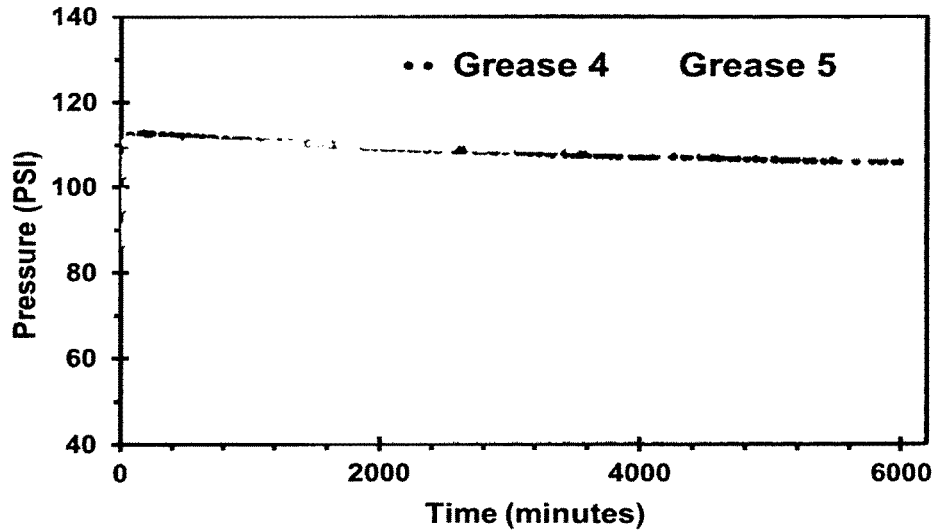

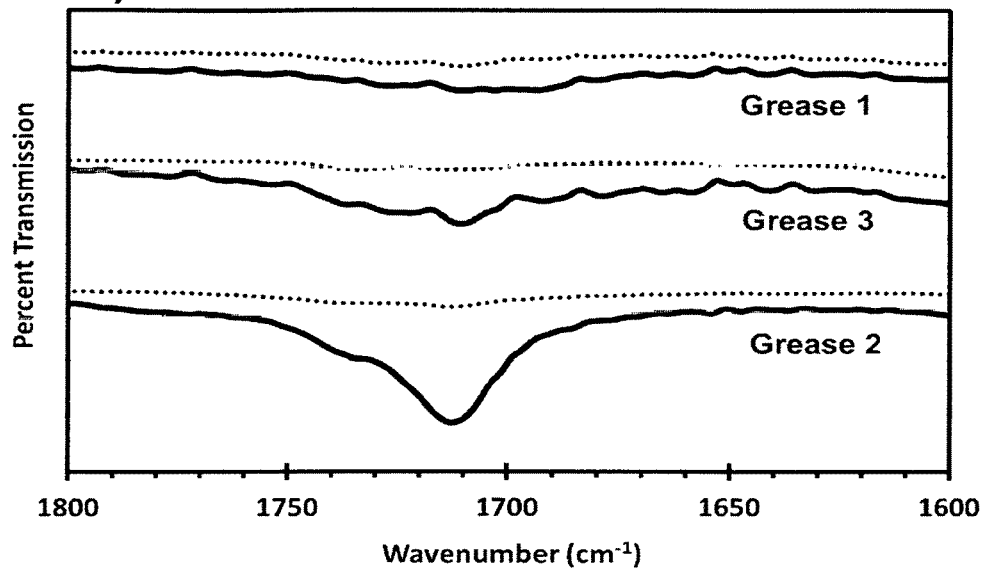
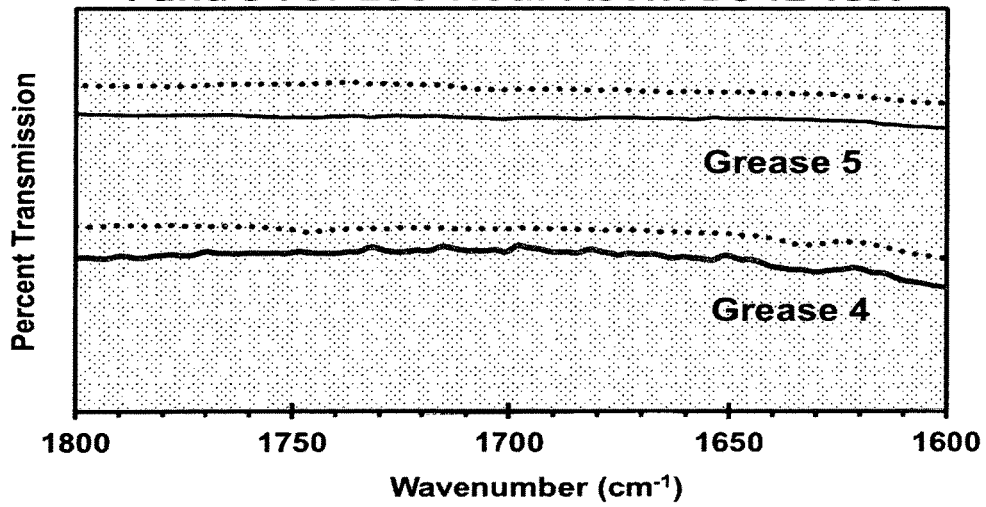

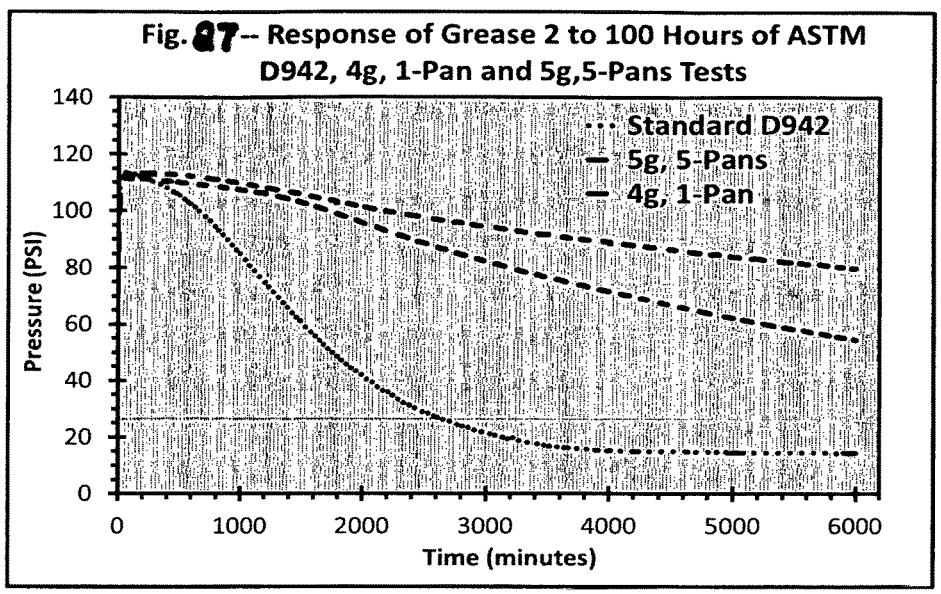
Fig. 27 -- Response of Grease 2 to 100 Hours of ASTM D942, 4g, 1-Pan and 5g, 5-Pans Tests
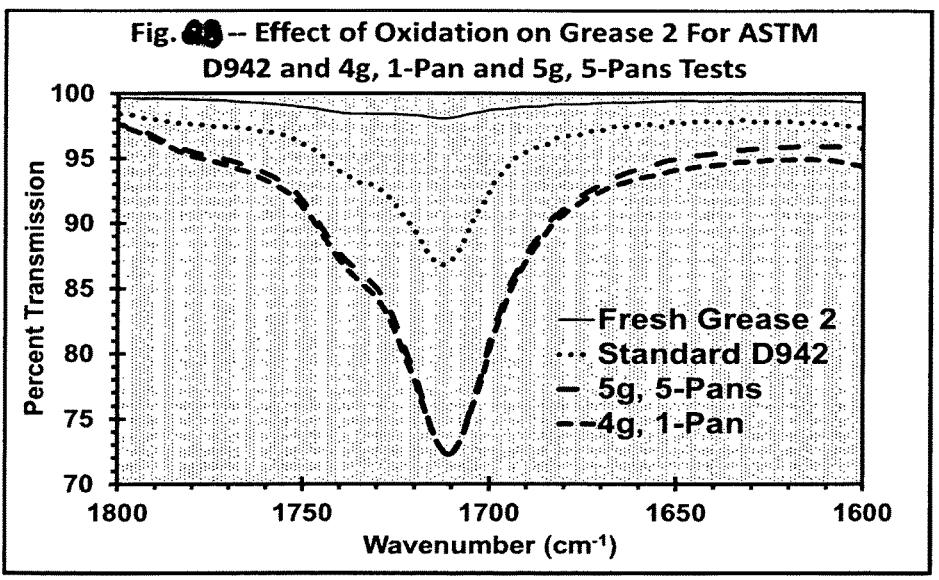
Fig. 28 -- Effect of Oxidation on Grease 2 For ASTM D942 and 4g, 1-Pan and 5g, 5-Pans Tests

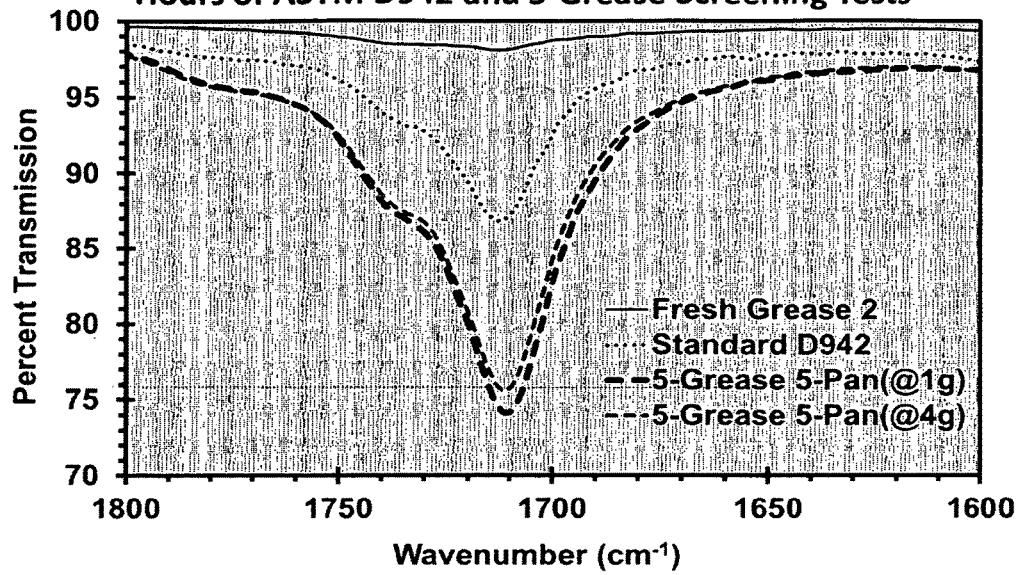
Fig. 29 -- Effect of Oxidation on Grease 2 For 100 Hours of ASTM D942 and 5-Grease Screening Tests
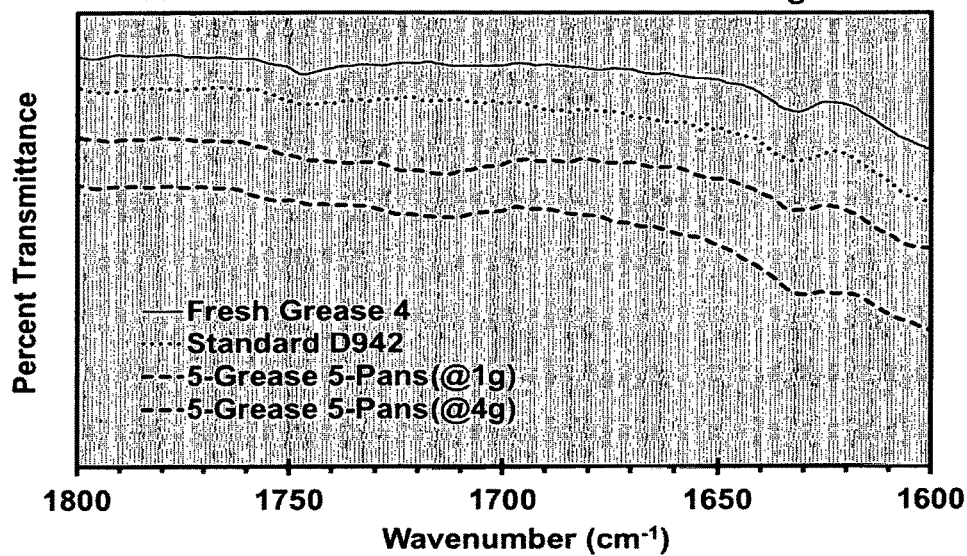
Fig. 30 -- Effect of Oxidation on Grease 4 For 100 Hours of ASTM D942 and 5-Grease Screening Tests

GREASE OXIDATION

This is a divisional under 35 USC 120 and 121 of U.S. patent application Ser. No. 14/121,952 filed on Nov. 6, 2014 A.D., which, as this in turn, claims benefits under 35 USC 119(e) of provisional application Nos. 61/962,464 filed on Nov. 7, 2013 A.D., and 61/965,160 filed on Jan. 24, 2014 A.D. The specifications of those three applications, to include their drawings, are incorporated herein by reference.

GENERALIZED OVERVIEW OF ART AND PURVIEW OF THE INVENTION

Grease oxidation resistance has always been an important aspect of its performance. Yet, because of its nature as a gelatinous colloidal dispersion in oil, understanding and improving this aspect of grease performance continues to be a technical challenge. Moreover, the wide range of components used to formulate this most ancient of blended lubricants, makes it difficult to devise bench tests that will accelerate grease response to oxidation conditions without loss of correlation with actual applications. This invention applies a combination of an advanced version of a test method that has been used for decades but with virtually no ability to compare greases. Precise control of test temperature and measurement of change in moderately high oxygen pressure is combined with infrared analysis of the grease after the test period of 100 hours. The technique has shown significant differences among greases common in lubrication. Apparatus is also of concern.

BACKGROUND TO THE INVENTION

As the most ancient of lubricants—said to extend back into the later Stone Age of man—grease is nonetheless perhaps the least understood and yet most widely used form of lubrication. This situation is not for want of effort to more clearly understand its response to operating conditions but more because of the wide range of those operating conditions and the range of components that over the millennia have been found to make it more usable.

A property having a major effect on the utility of grease is its resistance to oxidation and the consequences of this resistance on its ability to maintain an effective level of lubrication. Such resistance to oxidation and degradation under the stresses imposed by high temperatures and thousands of hours of operation has always been an important feature of grease performance, and a particular focus of its use and development over the years. As a consequence, increasingly advanced bench techniques have been developed to improve the understanding of both how the oxidation resistance can be enhanced by formulation and how this resistance can be lost in service.

Thus, oxidation stability is a very important property of lubricating greases. And so, any bench test capable of measuring this property is important to the degree that it is capable of predicting either the shelf-life or the service-life of a grease, or both.

Prior Art Grease Oxidation Test

In the 1940's the desire for a readily applicable bench test for quality control of a grease formulation by measuring its oxidation resistance led to the development and publication of ASTM Test Method D942 in 1947—a test method which became a standard and continues to be applied. Ref., ASTM Method of Test D942-02, "Oxidative Stability of Lubricating Greases by the Oxygen Pressure Vessel Method" (Reapproved 2007), ASTM Vol. 5, pp. 352-356, 2010; IP Method of Test 142/85 (92). It is routinely used to measure batch-to-batch grease oxidation stability, and also has been used in screening new grease formulations in development. That test requires exposure of 20 grams of a grease in five glass dishes with an exposed surface area of approximately 25 cm$^2$ per dish, thus 125 cm$^2$ per test. The dishes are stacked with an about 5-mm gap between them. Compare, FIG. 1. The combined stack of grease-filled dishes are then inserted into a cylindrical pressure chamber and exposed to oxygen of not less than 99.5% purity at an initial pressure of 100 pounds per square inch (PSI=690 kPa) and room temperature, which is then increased to 99±0.5° C. Under this increased temperature, the oxygen pressure is carefully released to maintain no more than 110±2 PSI. The test is typically continued for a chosen period of 100 or 200 hours, with resultant decrease in oxygen pressure as a result of grease oxidation taken as the test result.

Some Limitations of ASTM D942 as known in the Prior Art

Despite being relatively simple and straightforward, it is clearly stated in the ASTM D942 method that the test is severely limited in application to any other use than quality control of a grease formulation. For example, it is stated that the test should not be applied to compare the oxidation stability of the tested grease to actual behavior in service. Similarly, because of differences among grease formulations and the effects of oil volatility, comparison of oxidation resistances of different greases for a given application is also not recommended. Nor should the test be used to predict the stability of grease stored in containers or the oxidation stability of greases used in bearings and motors since only controlled oxidation of a physically stable surface of grease is used in the test.

Moreover, the ASTM D942 Test Method as known in the prior art is a very time consuming (100~500 hours) and labor intensive test requiring comparatively large sized samples. Thus, it is inapplicable to measuring small sample sizes taken from operating bearings or other applications to determine remaining oxidation resistance.

On the other hand, its simplicity is desirable. Perhaps an improved test may preserve this.

A SUMMARY OF THE INVENTION

Provided hereby is a significantly improved version of the ASTM D942 Test Method, with apparatus employable to effect the same. The same is useful in measurement of grease oxidation.

Hereby, the art is advanced in kind. The desirable simplicity and straightforward features of the ASTM D942 Test Method are retained, but its undesirable liquid bath and large sample size requirements are eliminated. Fourier Transform Infra Red (FTIR) analysis can be advantageously applied to extend the application of the ASTM D942 Test Method to comparative oxidation responses of greases. The FTIR can be equipped with Attenuated Total Reflectance (ATR). Beyond this, simultaneous analysis of several small grease sample sizes can extend the productivity of the present bench test and its methodology in determining grease oxidation resistance, and its utility is not limited to batch-to-batch uniformity of grease samples. Thus, much greater efficiency is gained, with reduced sample size as well as simultaneous evaluation of multiple grease samples. Moreover, the level of information obtained from the grease samples is increased, with more in-depth information on grease oxidation, which consequently allows comparison of the oxidation stability of various types of grease. Rapid screening using ASTM D942 type test conditions can be used to significantly increase the speed of acquiring information on oxidative stability of greases in the development process. A small footprint instrument is used.

Numerous further advantages attend the invention.

DRAWINGS IN BRIEF

The drawings form part of the specification hereof. With respect to the drawings, which are not necessarily drawn to scale, the following is briefly noted:

FIGS. 1-4b and 15-22 depict apparatus employed herein.
FIGS. 5-14 and 23-30 are graphs depicting results hereof.

ILLUSTRATIVE DETAIL

The invention can be further understood by the detail set forth below. As with the foregoing, the following, all of which may be read in view of the drawings, is to be understood in an illustrative but not necessarily limiting sense.

A First Illustration

ASTM D942 Type Tests using a Bath-Free RPVOT Instrument

At least one of the inventors considered that the physical configuration of the ASTM D942 test and grease oxidation exposure, coupled with subsequent analyses of the grease by FTIR had considerable merit if some way could be found to eliminate the need for the awkward and difficult-to-maintain oil bath. Fortunately, such a test instrument was available, and it was adapted.

In the last few years a new approach to meet ASTM Test Method the Rotating Pressure Vessel Oxidation Test (RPVOT) D2272, was developed. Ref., ASTM Method of Test D2272-02, "Oxidative Stability of Steam Turbine Oils by Rotating Pressure Vessel" (Reapproved 2011), ASTM Vol. 5, pp. 846-864, 2010; T. W. Selby, et al., "Studies of the Oxidation Dynamics of Turbine Oils—Initial Data from a New Form of the RPVOT," ASTM Symposium on Oxidation and Testing of Turbine Oils, Dec. 5, 2005, Norfolk, Va. See, U.S. Pat. Nos. 7,678,328 B1 and 8,679,405 B1—both incorporated herein by reference. This instrument, called the Quantum®, does not use a liquid bath to heat the pressure chamber. In essence, it is a bath-free isothermal instrument, which was first applied to the RPVOT method and incorporated into D2272 in 2009 after extensive round robin testing. Ref., ASTM D2272 Research Report RR:D02-1666.

A view of this instrument is shown in FIG. 2a as used for the RPVOT test. The design of the bath-free Quantum instrument also permits access to the test substance in the pressure chamber during test to extract a small sample. See, T. W. Selby, "Modern Instrumental Method of Accurately and Directly Measuring the Useful Life of Turbine Oils," OilDoc Conference, Feb. 1-3, 2011, Bavaria, Germany. See also, FIG. 2b.

Configuration of Quantum Instrument for Grease Oxidation Test

It was found that the Quantum instrument—which actually is an isothermal reactor capable of many uses—has all of the necessary geometry, heating, and availability of pressurized oxygen as a test condition. Therefore, it was adapted for running the ASTM D942 grease oxidation test.

Accordingly, a steel insert to reduce the inner volume of the Quantum instrument's pressure chamber and a vertical rack for the five grease samples are provided. These are shown in FIG. 3 with one of the grease-filled dishes. See also, FIG. 2b. To further simplify this alternative use of the instrument, simple steel shelving was configured into a pivotable, cradling framework that permitted the instrument to be tipped to a vertical position for use in grease oxidation tests or to set in its normal orientation for RPVOT tests. See, FIGS. 4a and 4b. See also, FIG. 2b.

In FIG. 4a, the Quantum instrument is set into the rotatable shelf to permit the operator to use it for the RPVOT test or for the grease oxidation test. In FIG. 4b, the shelf holding the Quantum instrument is tipped up to the position in which the pressure chamber within the instrument is vertical and the steel sleeve and rack of grease-containing dishes are installed awaiting sealing the lid and pressuring the closed chamber with oxygen.

Application of ATR Infrared

Infrared (IR) spectroscopy has been used for more than a half-century in the study of grease oxidation, starting with the work of Rappoport in 1952. E.g., O. Z. Pencheva and M. D. Tsonev, "Use of IR Spectroscopy in Research of Grease Oxidation," *Khimiya Teckhnollogiya Topliv i Masel*, 7 (July, 1973), 55-57; Z. M. Zhang, et al., "InfraRed Refractive Index and Extinction Coefficient of Polyimide Films," *International Journal of Thermophysics*, Vol. 19 (1998) 3, 905-915; G. Rappoport, Lubrication Engineering, Vol. 8 (1952) 129, 134. The introduction and development of FTIR spectroscopy was a major development permitting creative comparison of IR spectra. More recently, the use of ATR IR, particularly ATR FTIR, has further extended the use of IR to materials which are not very amenable to transmitting IR light through the sample to generate spectra. For greases, with their colloidal, gelatinous, and otherwise heterogeneous dispersion of components, ATR using only the reflective surface of the sample is a desirable comparative source of IR spectra.

Combined Analytical Technique to Compare the Oxidation Resistance of Greases

A test protocol was developed for 1) first determining the response of a grease to ASTM D942 using oxygen pressure decrease; then 2) sampling the grease in the dishes from the test; and finally 3) comparing the oxidation resistance of the greases using ATR FTIR spectra.

Results of ASTM D942 Tests of Five Greases using the Quantum Instrument

Applying the modified Quantum instrument shown in FIGS. 2b, 3, 4a and 4b, ASTM D942 grease oxidation tests were run for 100 hours and additionally, in some cases, 200 hours. Samples were not rotated. For each test, pressure change with time was continuously recorded. Following each test, the five dishes of grease were sampled for infrared analysis on an ATR equipped FTIR.

In first tests, it was found that there was essentially no difference among individual dishes from the five-dish stack. Consequently, only the top dish was sampled for subsequent IR analyses.

Grease #1

Tests using the ASTM D942 method were run for both a 100-hour and a 200-hour test period under this test method. FIG. 5 shows the closely similar pressure traces obtained during these tests. Grease #1 was run at both 100 hours and 200 hours for comparison of both 1) the repeatability of the pressure-decrease curves in the first 100 hours; and 2) the continuing rate of oxidation for the next 100 hours of exposure.

It is evident that the oxidation curves are quite similar and that ASTM Method D942 as applied by the modified Quantum instrument is capable of providing reproducible information. The oxygen pressure in Test 1 at 100 hours was 96 PSI. At 200 hours of test it was 86 PSI.

Grease #2

ASTM D942 tests were conducted in replicate for 100 hours on Grease #2. Results are shown in FIG. 6.

The response to ASTM D942 was quite strong but highly repeatable. This grease may have begun oxidizing even before the chamber temperature reached its maximum of 99° C. Interestingly, the final pressures in the chamber showed total oxygen uptake during test by dropping to atmospheric pressures of about 15 PSI.

Grease #3

As mentioned earlier, according to the protocol of ASTM Test Method D942, when the oxygen pressure rises to 110±2 PSI, the oxygen is carefully released to keep it at this level until oxidation of the grease begins. FIG. 7 suggests the consequences of not relieving the oxygen pressure in Test 1 for almost 2½ hours.

The data indicate that additional grease oxidation may occur under such preliminarily higher oxygen pressure. Final oxygen pressures were 96 PSI after 100 hours for Test 1 and 91 PSI after 200 hours for Test 2.

Grease #4

Grease #4 was found to be highly resistant to oxidation in the D942 test as shown by the three replicate tests in FIG. 8. In these three tests, the lowest oxygen pressure after a 100-hour test was only 107 PSI.

Grease #5

Evaluation of Grease #5 shown in FIG. 9 indicated this grease to also be fairly resistant to oxidation over 100 hours of test.

ATR-FTIR Analyses of Greases Oxidized Hereby

Following exposure of each of the foregoing five greases to the present modified type ASTM Method D942 for 100 or more hours, the oxygen pressure is released. When the pressure chamber is sufficiently cooled, the instrument is opened, and the rack of dishes is removed.

About 2-4 milligrams of grease sample was needed in analyzing its FTIR spectrum using the ATR. For consistency in the study, the grease sample was skimmed from the surface of the grease in the top plate.

ATR-FTIR Analysis of Grease #1

As shown in FIG. 5, Grease #1 was subjected to 100 and 200 hours oxidation exposure in ASTM Method D942 run in the modified Quantum instrument.

FIG. 10 shows an analysis of the spectrum of fresh Grease #1 from a wavenumber of 1600 to 2200 $cm^{-1}$. Values of the percent transmittance of only the fresh Grease #1 are shown on the left-hand ordinate. On the right-hand ordinate, the FTIR values of percent transmittance for the oxidized grease samples are subtracted from those of the fresh grease (in this case Grease #1). This shows the effects of oxidation on the fresh test grease by the increase in concentration of oxidized grease components and thus a decrease in percent transmittance.

It is evident and confirming that at the wavenumbers between approximately 1700-1750 $cm^{-1}$ associated with carbonyl oxidation products (carboxylic acids, ketones, aldehydes, etc.) there is, as would be expected, substantial increase as a consequence of oxidation. Moreover, greater oxidation is shown in the 200-hour test compared to that of 100 hours. Interestingly, even in the fresh grease, there are evident peaks shown in the vicinity of 1700-1750 $cm^{-1}$. This suggests that the formulation of this grease may contain carbonyl additives components or that the grease may experience some oxidation in formulation.

ATR-FTIR Analysis of Grease #2

As discussed in Section 3.2 and shown in FIG. 6, Grease #2 was very oxidation susceptible in the ASTM D942 oxidation test protocol. The three curves shown in FIG. 11 resulted after the grease was tested twice and the resulting FTIR spectra subtracted from that of the fresh Grease #2. The peaks of Test 1 and Test 2 are both at 1710 $cm^{-1}$ with reduced percent transmittance of 17% and 11%, respectively, at this wavenumber closely associated with hydrocarbon oxidation.

ATR-FTIR Analysis of Grease #3

Grease #3 demonstrated oxidation susceptibility in FIG. 7. In this, it is similar to Grease #1. As shown in FIG. 12, however, when the FTIR spectra were obtained, the degree of oxidation shown by the decrease in percent transmission was somewhat greater than Grease #1.

ATR-FTIR Analysis of Grease #4

As expected from FIG. 8, in FIG. 13 Grease #4 shows high oxidation resistance. The three tests run at 100 hours show some variability in the oxidation wavenumber region indicating a sensitive antioxidant.

ATR-FTIR Analysis of Grease #5

From the ASTM D942 oxidation tests, Grease #5 also seems resistant to oxidation. This becomes clear in FIG. 14. Essentially, no oxidation is shown by Grease #5. Moreover, in some distinction to Grease #4, the four tests on Grease #5 are fairly similar.

Discussion

As virtually the most ancient form of man-made lubricant, grease has been unique in its complex forms and the nature of its tribological contributions. Grease is subject to many forms of stress in providing lubrication. One of the more important of these is oxidation. This is particularly the case since, in many applications, the grease is very exposed to the environment composing and surrounding the lubrication site—however varied that environment may be. Moreover, unlike forms of liquid lubrication, there is seldom much that can be done to some degree of protect the grease from its often harsh environment. As a consequence of the complex chemistry and composition of greases, and the variable nature of the environment in which given grease is applied, standard bench tests of the chemical performance of greases such as ASTM D942 are infrequent. This is in contrast to the more commonly employed physical bench tests for wear and physical degradation in service. It was for this reason that the application of ASTM D942 was chosen for improving its instrumental simplicity and heating control and removing its stated interpretive limitations mentioned above.

Results of this illustration showed clearly that among the five greases studies, the combination of ASTM Method D942 and the subsequent FTIR analysis of the spectra of the original grease compared to the grease after oxidation showed that the FTIR information supported the relatively simplistic information of ASTM D942 alone. Moreover, the limitations of ASTM D942 when used alone were overcome with the sharper information provided by the FTIR analysis.

Some Conclusions

On the basis of the foregoing, it would seem reasonable that the ASTM Method D942 should be extended to include the use of FTIR analysis. With such information the ASTM Method could be used to show correlation with field experience and to also permit selection of better additives for specific applications. The use of the FTIR spectrum subtraction technique shown herein was helpful in more clearly discriminating the changes in different greases brought about by oxidation.

A Second Illustration

Use of FTIR

As above, a modern FTIR instrument was equipped with ATR. Thereby, a technique for oxidation measurement that combines the ASTM D942 test with FTIR analysis overcomes the limitations of the original ASTM D942 test. The combination of FTIR with ASTM D942, referred to in this illustration the Advanced Technique, would provide much more in-depth information on grease oxidation which would consequently allow comparison of the oxidation stability of various types of grease.

It was found initially that sufficient information could be obtained from IR of the surface of the grease samples. This led to the consideration of using much smaller grease sample in the pans and, thus, the ability of applying the principles of D942 and FTIR to samples having the same surface area in the test, but much less grease mass. This approach would not produce the same oxygen pressure decrease, but the FTIR oxidation information would be the same.

This led to an additional test concept in which it was considered that rapid screening of grease or additive formulations based on oxidation resistance should be possible. The screening technique uses the ASTM D942 test conditions to oxidize grease; however, IR analysis is used primarily to measure oxidation resistance of the sample. This method can be used to significantly increase the speed of acquiring information on oxidative stability of greases under development.

Grease Oxidation Measurement Techniques

This second illustration builds upon the first illustration. That illustration compared the oxidation resistance of several greases of varying oxidation resistance.

As before, the experimentation of this illustration was carried out in a specially modified iso-thermal reactor normally used in determining oxidation resistance of liquid lubricants per ASTM D2272. FIGS. 2a and 4b show the instrument before and after a modification that permits the instrument to be used alternatively in either test configuration. An advantage of modifying the iso-thermal reactor to conduct the ASTM D942 test was that it did not require the care and concerns of a liquid bath as the sample chamber is heated by electrical resistance. A stainless steel insert, e.g., FIGS. 2b, 3, 15, was used to obtain the appropriate chamber volume for ASTM D942 testing. Other accessories, including a sample rack and sample pans were provided to comply with the method, and are shown in FIG. 3. The same test setup was utilized in the present illustration.

Application of the modified iso-thermal reactor for the ASTM D942 method was validated in the first illustration by testing multiple grease samples for 100 and 200 hours. Samples were not rotated. Consistent results were obtained from repeat tests and show good agreement with ASTM D942 tests run at an external laboratory with standard test equipment. All results were within the method's repeatability and reproducibility.

Again, according to the ASTM D942 Test Method, 20 g of a grease sample is tested in five glass dishes with an exposed surface area of approximately 25 cm$^2$ per dish and a total surface area of 125 cm2 per test. The dishes are stacked with a gap of approximately 5 mm between them. The combined stack of grease-filled dishes are then inserted into a cylindrical pressure chamber and exposed to oxygen of not less than 99.5% purity at an initial pressure of 100 pounds per square inch (PSI) and room temperature which is then increased to 99±0.5° C. Under the increased temperature, the oxygen pressure is maintained at 110±2 PSI.

The test is continued for a chosen period of time and decrease in oxygen pressure resulting from grease oxidation is reported in PSI as the test result.

Five lithium based greases of varying oxidation resistance were chosen for the current work. Greases 1, 2 and 3 are developmental greases provided by Loadmaster Lubricants LLC, interested in extending the information gained from ASTM D942. Greases 1, 2 and 3, respectively, are said to be high load-carrying lithium grease, fully synthetic lithium complex grease and high load carrying lithium complex grease. Greases 4 and 5 are commercial lithium-complex greases and the compositions are proprietary.

Advanced Technique for Oxidation Measurement

Again, IR spectroscopy has been used for over half a century in the study of grease oxidation. E.g., G. Rappoport, *Lubrication Engineering*, vol. 8 (1952); O. Z. Pencheva et al., "Use of IR Spectroscopy in Research of Grease Oxidation," *Khimiya Teckhnollogiya Topliv i Masel*, Vol. 7 (July, 1973); Z. M. Zhang, et al., "Infrared Refractive Index and Extinction Coefficient of Polyimide Films," *International Journal of Thermophysics*, Vol. 19 (1998); P. M. Cann, et al., "Grease Degradation in ROF Bearing Tests," *Tribology Transactions*, Vol. 50 (2007); S. Hurley et al., "Infrared Spectroscopic Characterization of Grease Lubricant Films on Metal Surfaces," *NLGI Spokesman*, Vol. 64 (October, 2000). The level of oxidation in petroleum-based lubricants in general is measured in the carbonyl region (1670 to 1800 cm−1). IR energy is absorbed in this region as a result of the carbonyl group (C=O) stretch from various carbonyl compounds including, ketones, esters, carboxylic acids, carbonates, aldehydes, anhydrides and amides. The FTIR peak around 1715 cm$^{-1}$, generally known as the "oxidation peak," results from C=O stretch and indicates breakdown of the lubricant and formation of oxidation by-products.

Combining the ASTM D942 method with IR analysis is a dependable approach to grease oxidation measurement. The following steps were used in the technique:

1) Response of a grease to ASTM D942 is determined by measuring change in oxygen pressure in 100 hours.
2) The grease is sampled from the pans after the test.
3) Oxidation resistance of the grease is analyzed using ATR-FTIR spectroscopy.

For this illustration a PerkinElmer Spectrum 100 FTIR Spectrometer equipped with a universal ATR sampling accessory was employed. The latter was indispensable in applying IR to opaque materials by using the reflection from the sample surface. IR analysis was conducted using an about 2-4 mg sample. Multiple IR spectra taken from the same sample showed no measurable difference in the resulting spectra, which indicated that effects of the small variation in sample size is negligible. Sample was skimmed from the surface of the grease.

Screening Technique

Attempts have been made in the past to design a simple and rapid screening test based on grease oxidation stability that correlates well with in-service oxidation conditions. Ref., W. W. Bailey et al., "Dynamic Oxidation Stability of Lubricating Greases," *NLGI Spokesman*, Vol. 15 (April, 1982). In this illustration, a test concept has been developed for rapid screening of grease samples based on oxidation resistance. The concept is similar to the High Throughput Screening (HTS) technique used in drug discovery.

In the HTS process for drug discovery, biological targets are identified and potential compounds are screened against the target. This was originally an expensive, tedious, and time-consuming manual process, which has been termed Low Throughput Screening (LTS), which usually took months. Over the last two decades, innovations in technology transformed the LTS into an automated microprocessor controlled robotic process, i.e., HTS. This quantitative step makes it possible to screen 10,000-100,000 compounds within 24 hours.

A Screening Technique similar to HTS may be useful to speed up the grease development process. As the ASTM D942 Method requires five sample pans, it was considered that a possibility that five different greases in the same test could be evaluated. The screening technique does not need to be limited to five grease samples. Initially, five greases were chosen mainly because the current ASTM D942 Test Method setup is equipped with five sample pans. The setup can be easily modified to test any reasonable number of greases at the same time, as an illustration, say, from one to about twenty, to include about from two or three to ten or fifteen, and about from four to seven or eight.

The screening test concept was evaluated in the following two steps.

Step 1: Reduced Sample ASTM D942 Type Test

A modified ASTM D942 test with smaller sample amounts was evaluated using Grease 2. Four and five grams of Grease 2 were tested in the following two configurations:
1) 5 g, 5-Pan Test: five pans, each containing 1 g of Grease 2, were tested in the iso-thermal reactor for 100 hours following the D942 test conditions (99° C. and 110-PSI initial pressure).
2) 4 g, 1-Pan Test: one sample pan, containing 4 g of Grease 2, was tested in the same way.

Grease 2 was spread out in each pan, and the surface was leveled using a clean spatula to minimize the impact of any differences in surface area between pans. Following the 4 g, 1-Pan and 5 g, 5-Pan Tests, 2-4 mg of Grease 2 was sampled for IR analysis.

Step 2: HTS Test

Next, a screening test concept was developed where five different greases were oxidized simultaneously under ASTM D942 type test conditions, and then oxidation resistance of the greases was measured by IR analysis. The screening technique uses the Quantum test equipment to oxidize the grease samples; oxidation, however, is measured primarily by IR analysis. The following two configurations were evaluated:
1) 5 grease-5 pan @1 g: 1 g each of the 5 grease samples was tested in the iso-thermal reactor for 100 hours at the D942 test conditions (99° C. and 110-PSI initial pressure).
2) 5 grease-5 pan @4 g: 4 g each of the 5 greases was tested in the same way.

The grease samples were spread out in the pans, and the surfaces were leveled using a clean spatula to minimize the impact of any differences in surface area between the pans.

As would be expected, oxygen uptake during the 5 grease tests does not correlate with the oxidation stability of the individual grease samples. The 5 grease screening test disregards the change in pressure generated by the oxidation process and utilizes IR analysis to assess the extent of oxidation of the grease samples.

Results

Results obtained are set forth below.

Standard ASTM D942 Type Test

Utilizing the Quantum iso-thermal reactor, each of the five greases was subjected to 100 hours of the standard D942 Test conditions.

FIG. 23 shows overlay of pressure vs. time plots for Greases 1, 2 and 3. Greases 1 and 3 show relatively small changes in pressure in 100 hours compared to Grease 2. The results indicate that Greases 1 and 3 are relatively resistant to oxidation. In contrast, Grease 2 appears to be highly susceptible to oxidation as the chamber pressure reduced to atmospheric level of about 15 PSI as a result of complete oxygen uptake during the 100-hour ASTM D942 test.

FIG. 24 shows the responses of Greases 4 and 5 to 100-hour ASTM D942 tests. A very small change in pressure was observed for both of the greases indicating that these greases are highly resistant to oxidation. Table 1 below compares the changes in oxygen pressure for all five grease samples during the ASTM D942 type tests.

TABLE 1

| 100-hour ASTM D942 Oxidation | | | | | |
|---|---|---|---|---|---|
| | Grease 1 | Grease 2 | Grease 3 | Grease 4 | Grease 5 |
| Pressure Drop (PSI) | 14.4 | 95.0 | 13.5 | 6.0 | 2.8 |

Advanced Technique

In the advanced technique, the grease samples oxidized by 100-hour ASTM D942 type test were analyzed by FTIR-ATR. Initially, each of the five dishes of grease from the ASTM D942 type test was sampled for IR analysis. No significant differences were observed between the dishes from the five-dish rack. In subsequent tests, only the top dish was sampled for IR analysis.

The IR peak around 1715 $cm^{-1}$, known as the "oxidation peak," was evaluated to measure the extent of oxidation in the five greases following individual 100-hour D942 tests. FIG. 25 compares the ATR-FTIR spectra from Greases 1, 2 and 3 following oxidation by 100-hour ASTM D942 type tests. Intensity of the oxidation peak is higher for all three greases after the ASTM D942 tests compared to the fresh grease samples. The IR analysis clearly indicates oxidation of the grease samples; the level of oxidation, however, is substantial for Grease 2 compared to the other two greases. As observed previously in FIG. 24, the change in oxygen pressure for Grease 2 during the 100-hour ASTM D942 type test was also much higher compared to Greases 1 and 3. FIG. 26 compares IR spectra of fresh and oxidized Greases 4 and 5. No oxidation peak is observed in either grease before or after the 100-hour ASTM D942 type test. As discussed above, both of these greases produced very little change in pressure during the 100-hour ASTM D942 type tests.

Therefore, IR analysis agrees well with ASTM D942 type test results, which confirms that Grease 2 is highly susceptible to oxidation, Greases 1 and 3 are moderately stable, and Greases 4 and 5 are extremely resistant to oxidation under similar oxidative conditions.

The results also support the approach of using IR analysis as an alternate way to measure grease oxidation stability. The combination of ASTM D942 test method and the subsequent FTIR analysis evidently enhances the relatively simplistic information provided by ASTM D942 test alone. Moreover, the limitations of ASTM D942 test when used alone are overcome with the more in-depth information provided by infrared analysis.

Reduced Sample—D942 Type Tests

FIG. 27 shows a comparison of the responses of Grease 2 to ASTM D942 type, 4-g, 1-Pan and 5-g, 5-Pan tests, where each test was conducted for 100 hours. Five grams of Grease 2 distributed in five sample pans were evaluated in the 5-g, 5-Pan test whereas only one sample pan containing 4 g of Grease 2 was evaluated in the 4-g, 1-Pan test. As observed in FIG. 27, an ASTM D942 type procedure produces a pressure loss of 95 PSI for this grease, which is significantly higher compared to 56.9 and 32.7 PSI obtained during the 4-g, 1-Pan and 5-g, 5-Pan tests, respectively.

The results clearly indicate a correlation between the change in pressure during these tests with the volume of oxygen available per mass of sample grease. Table 2 compares the results of the ASTM D942 type test with 4-g, 1-Pan and 5-g, 5-Pan tests on Grease 2.

TABLE 2

100-hour Oxidation of Grease 2

|  | Standard type D942 | 5 g, 5-Pan | 4 g, 1-Pan |
| --- | --- | --- | --- |
| Pressure Drop (PSI) | 95.0 | 56.9 | 32.7 |

FTIR spectra taken from Grease 2 following the standard type ASTM D942 and the 4-g, 1-Pan and 5-g, 5-Pan tests are compared in FIG. 28. The modified tests with reduced sample mass caused a higher level of oxidation in Grease 2 compared to the standard type ASTM D942 test. IR analysis clearly shows that the standard type ASTM D942 test does not completely oxidize Grease 2 during the 100 hours.

It is apparent in these results that the standard type ASTM D942 test leaves Grease 2 partially oxidized, which is caused by complete exhaustion of oxygen in the reaction chamber before the test ends, whereas the reduced sample tests allow further oxidation of the grease. The ratio of oxygen volume in the chamber to the sample mass is higher in case of the latter.

Incomplete information is likely obtained from the standard type ASTM D942 test for greases that are highly susceptible to oxidation. The results demonstrate another limitation of the ASTM D942 method, as well as the significance of coupling the test with IR analysis.

Screening Test

As discussed above, there was considerable agreement between the test results obtained by the standard type ASTM D942 test and the Advanced Technique. In an effort to develop a Screening Test concept, the five greases were tested simultaneously in the following two configurations: 5-grease, 5-pan Test (@1 g) and a 5-grease, 5-pan Test (@4 g).

FIG. 29 compares the effect of oxidation on Grease 2 for the standard type ASTM D942 test, 5-grease, 5-pan (@1 g) and 5-grease, 5-pan (@4 g) screening tests where each test was conducted for 100 hours. The screening tests clearly obtained a higher level of oxidation of this sample compared to the standard ASTM D942 type test, as measured by IR analysis. Both the standard type ASTM D942 test and the screening tests found Grease 2 to be highly susceptible to oxidation compared to the other four greases.

As observed in FIG. 30, IR analysis detected no oxidation of Grease 4 after the standard type ASTM D942 test; a minimal level of oxidation, however, was measured in the same grease after the Screening Tests. Both tests indicated that Grease 4 is highly resistant to oxidation. The results imply that the 5-grease test creates a relatively harsh oxidative environment compared to the standard type test, which is designed to measure oxidation of a single grease sample.

The preliminary results obtained in this illustration demonstrate that the screening test concept can be useful in rapid selection of grease or additive formulations. This approach could significantly reduce the time needed for grease research and development.

Some Conclusions

ASTM D942 is severely limited in its applications to any other use than quality control in grease manufacturing processes. The goal of this illustration was to improve the ASTM D942 Test Method, by combining precise control of test temperature and measurement of oxygen pressure with IR analysis, and that goal was met. The in-depth information provided by FTIR analysis expands the applications of the original method. The extended test is capable of comparing oxidation stability of various types of grease. Based on this analysis, the ASTM D942 test should be extended to include the use of IR analysis.

In addition, a screening test concept was developed. This involved simultaneous oxidation of multiple grease samples under ASTM D942 conditions and measurement of oxidation resistance by IR analysis. The results indicated that the screening test and the standard ASTM D942 Test Method measure comparable oxidation tendency of the grease samples. The screening test can be useful in selecting preliminary formulations in the grease development process by significantly shortening the analysis time.

Pivotable, Cradling Framework, and Accessories

The pivotable, cradling framework can hold the bath-free, isothermal, bomb instrument, especially embodied as a Quantum instrument, which is an embodiment of a rotatable bomb as of the incorporated patents, U.S. Pat. Nos. 7,678,328 B1 and 8,679,405 B1. It can permit the cylindrical chamber of the rotatable bomb instrument to be tipped to a vertical position with respect to its cylindrical chamber axis from an orientation in which the cylindrical chamber is acutely angled with respect to a supporting surface such as a bench top when the rotatable bomb instrument has its bottom parallel with the bench top. Compare FIG. 2a with FIGS. 2b, 4a and 4b. See also, FIGS. 21 and 22. Further, the pivotable, cradling framework and other accessories can have such features as found in FIGS. 15-22, as follows:

FIG. 15 depicts four views of a grease vessel insert, i.e., a hollow, annular type, cylindrical insert, which also may be known as a volume reducer, for the cylindrical chamber of the rotatable bomb instrument. It can be made, for example, of #304 stainless steel with a #62 surface finish. Other materials may be employed.

FIG. 16 is a side view of a volume reducer lifting handle, for example, to lift the grease vessel insert. It can be made, for example, of a 0.110-inch stainless steel spring wire. Another size or material may be employed.

FIG. 17 depicts two further views of a dish holder assembly for vertically stacking dishes, which may also be known as pans, for holding up to five grease samples, for example, one sample per dish. Such an assembly may be configured to hold more or less dishes, as alluded to above.

FIG. 18 depicts two views of a dish holder stand shelf that may be found in the assembly of FIG. 17. It is made, for example, of #304 stainless steel with a #62 surface finish. Another material may be employed.

FIG. 19 depicts two views of a dish holder stand shelf that may be found in the assembly of FIG. 17. It is made, for example, of #304 stainless steel with a #62 surface finish. Another material may be employed.

FIG. 20 depicts three views of a lifting tab for a dish holder stand that may be found in the assembly of FIG. 17. It is made, for example, of 0.025-inch #304 stainless steel with a #62 surface finish. Another size or material may be employed.

FIG. 22 depicts a number of views of a stand, i.e., the pivotable, cradling framework, for a grease oxidation device hereof, for example, the Quantum instrument, of which sides are found in FIG. 21. It is made of "UNOBTANIUM" material and has a #62 surface finish.

FURTHER DISCLOSURE

Figure 2B:
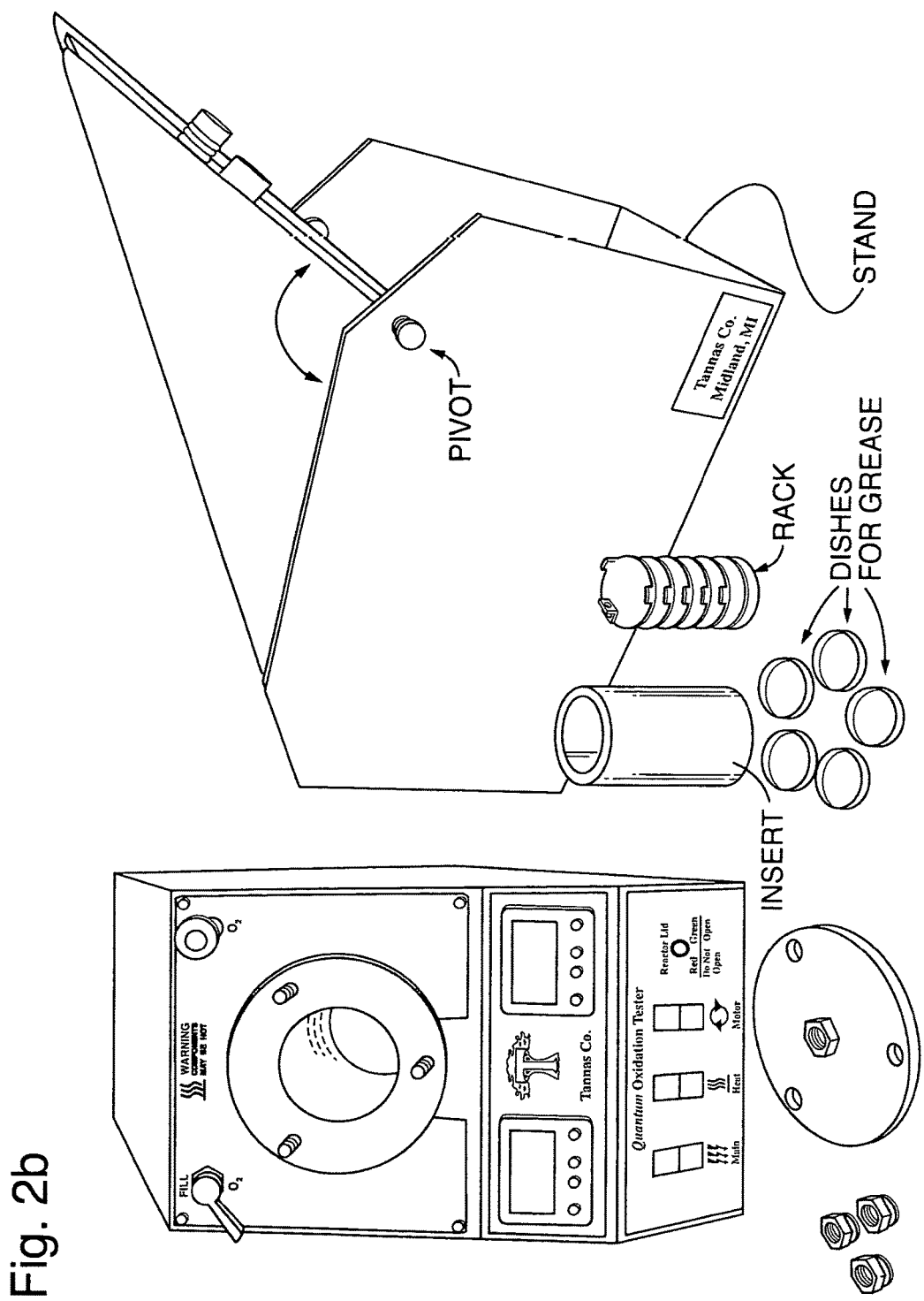
Figure 3:
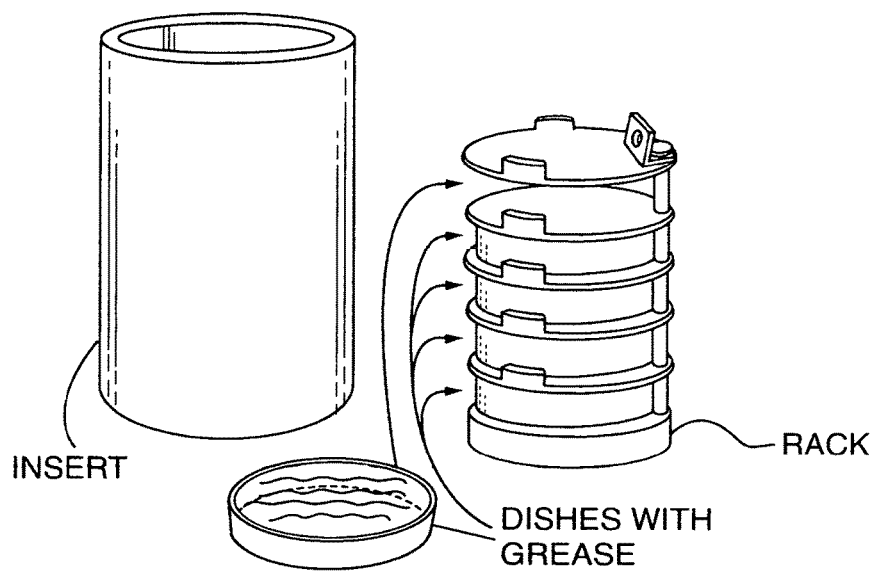
Figure 4A:
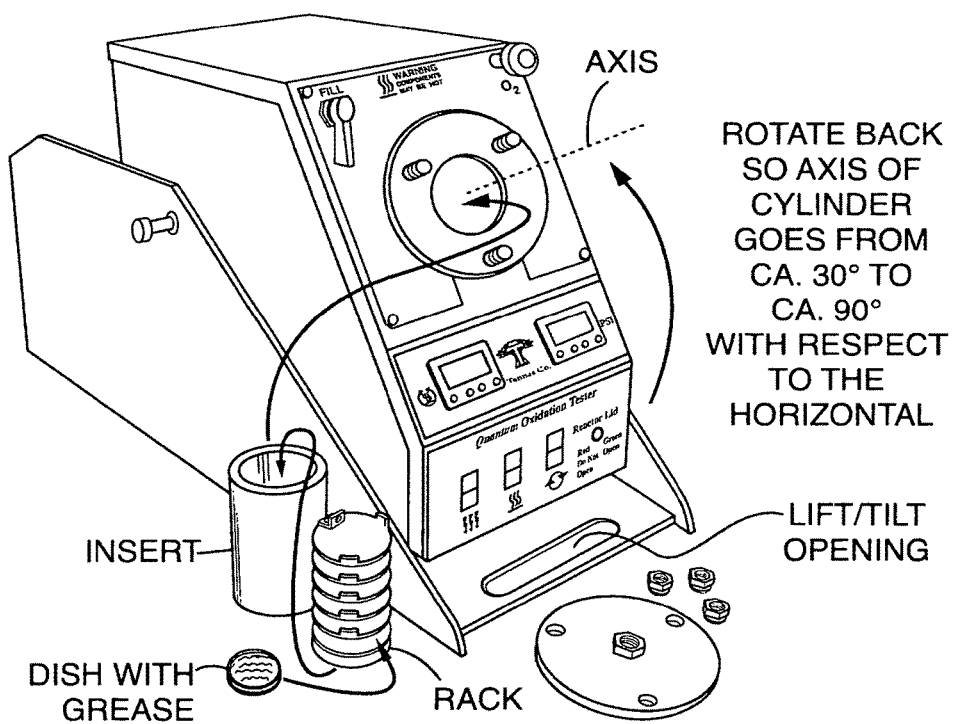
Figure 15:
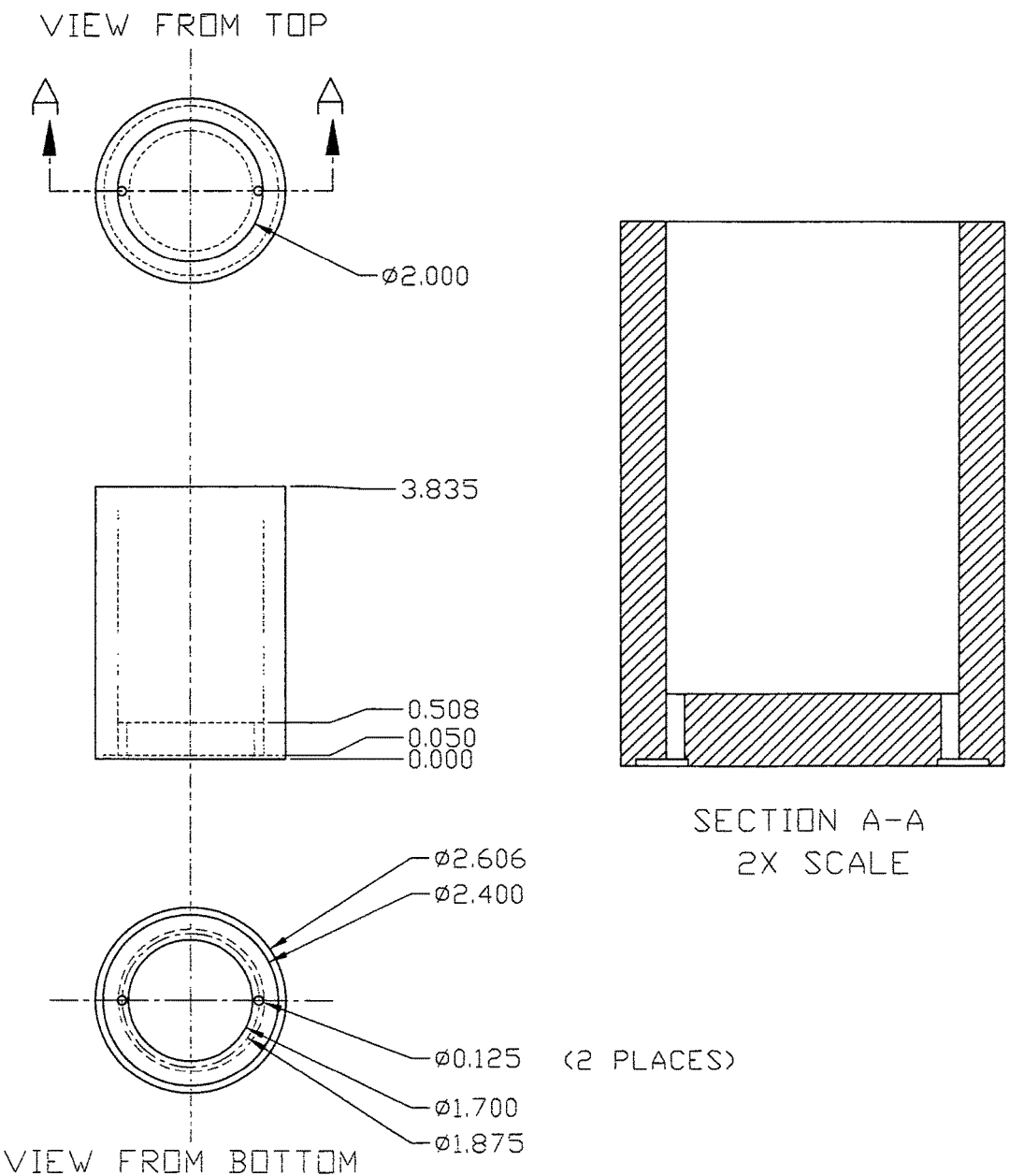
Figure 16:
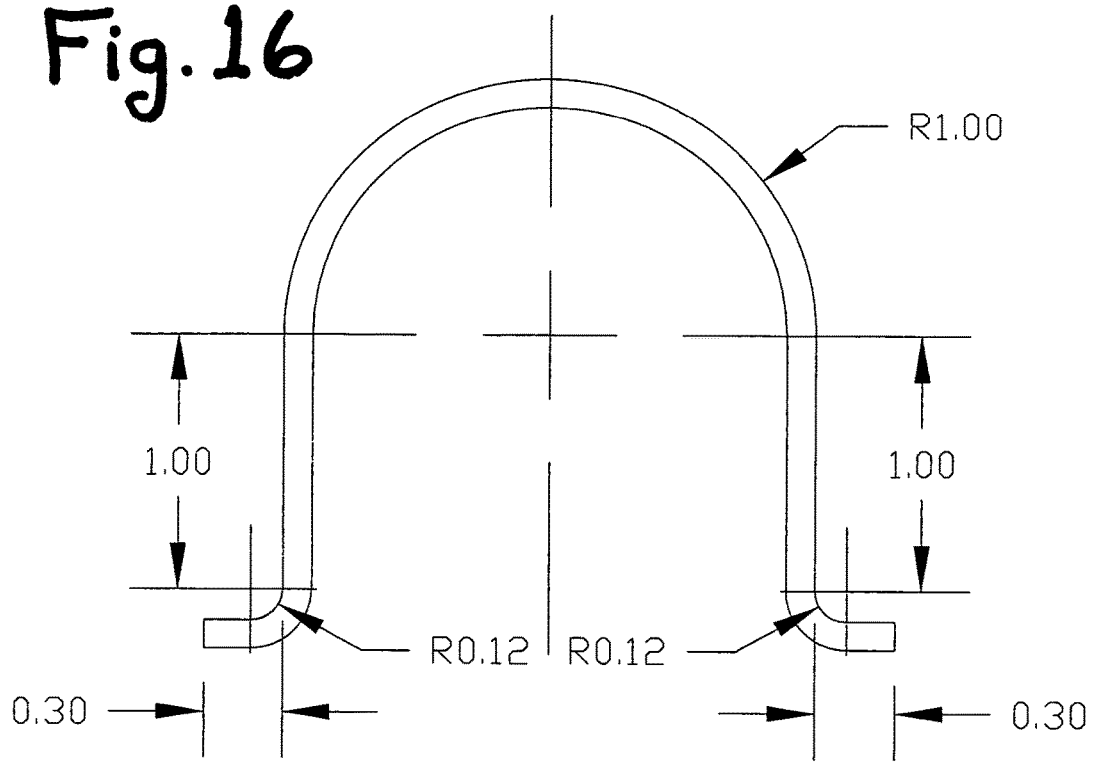
Figure 17:
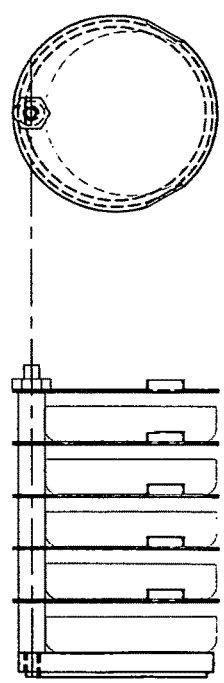
Figure 18:
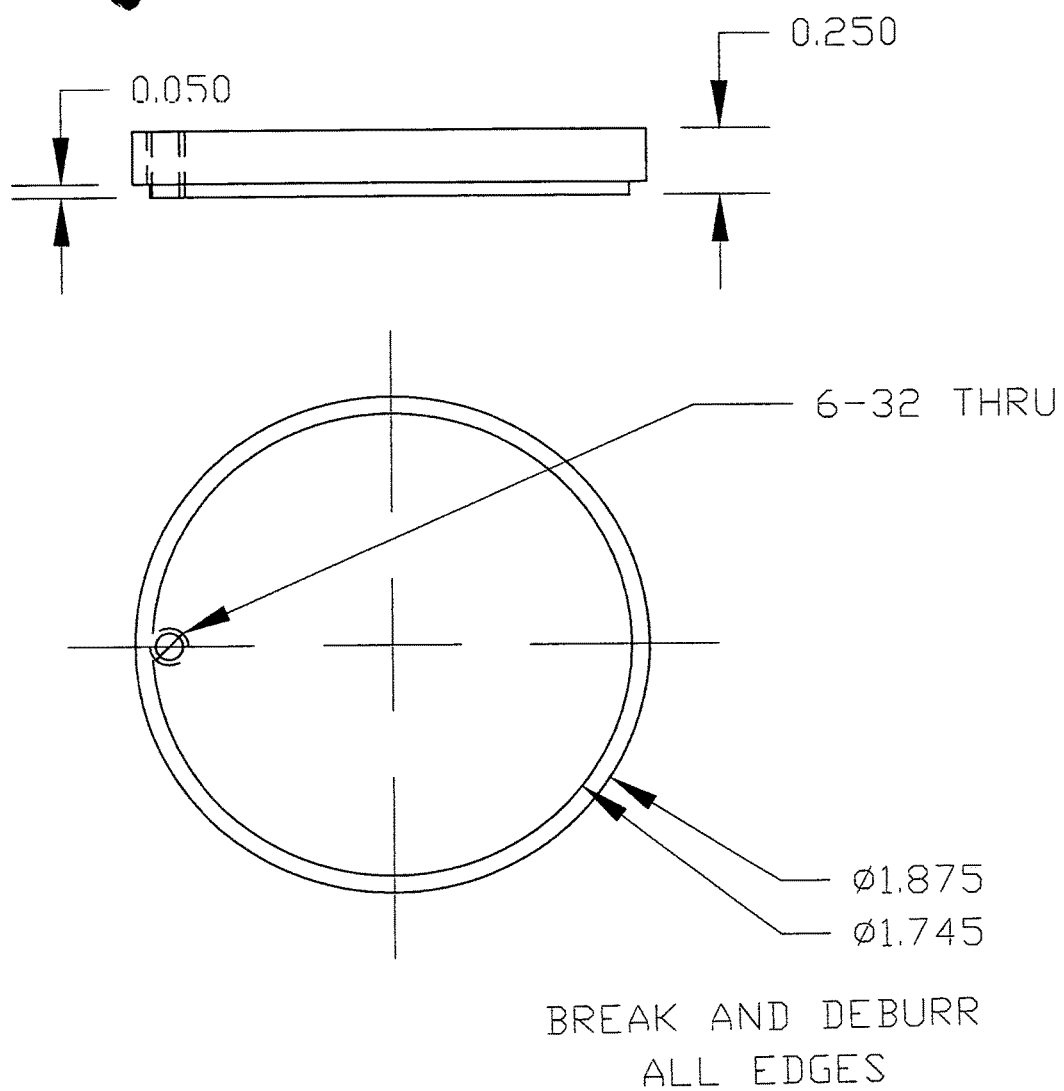
Figure 19:
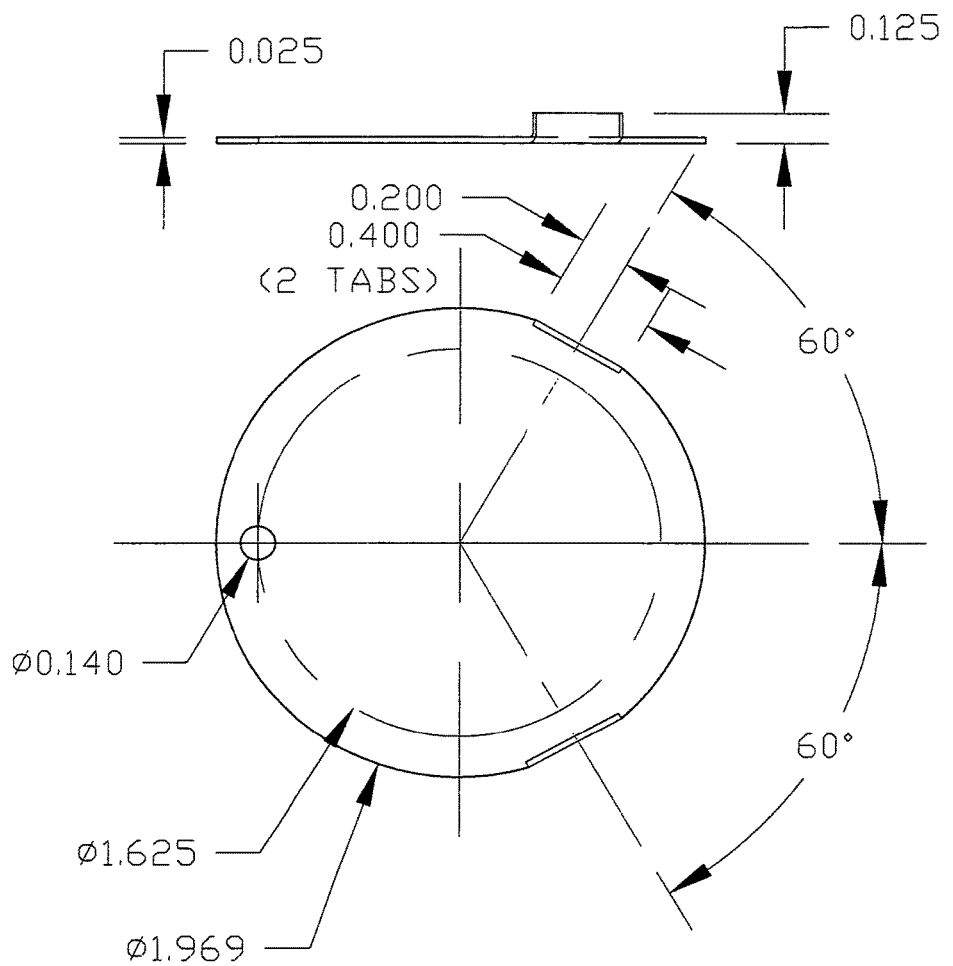
Figure 20:
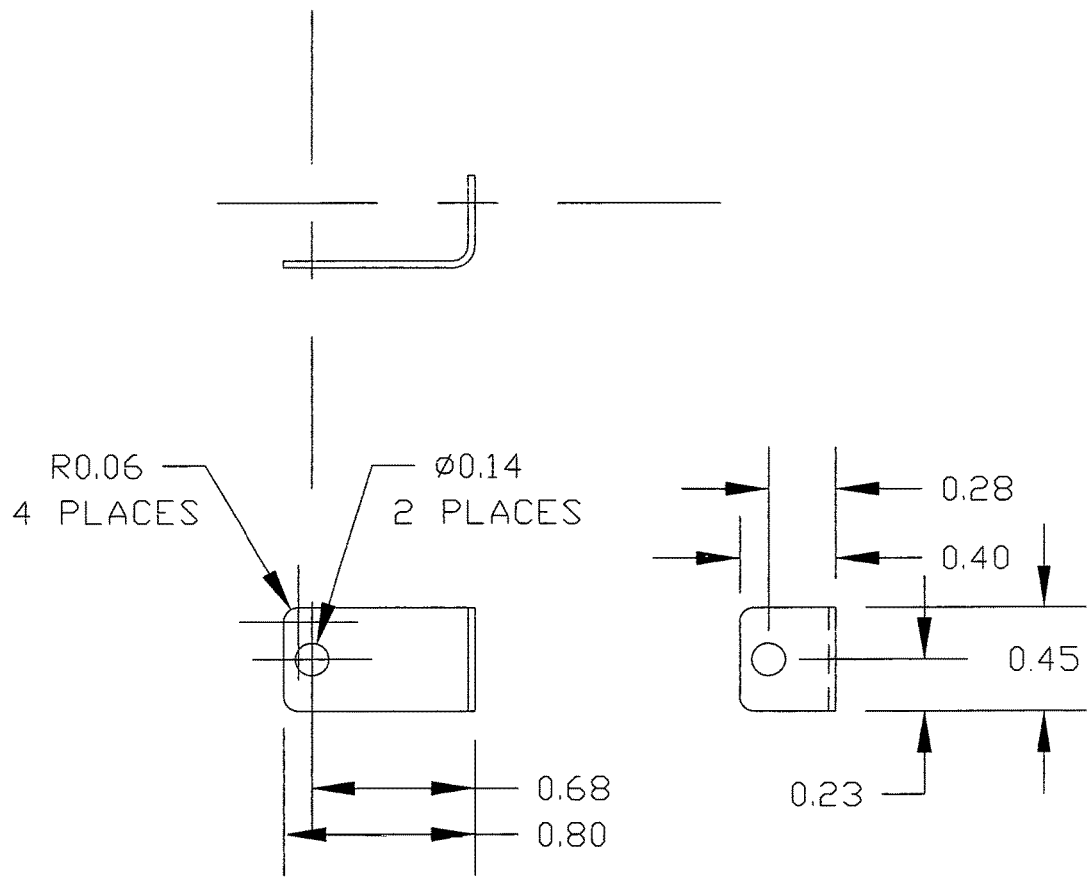
Figure 21:
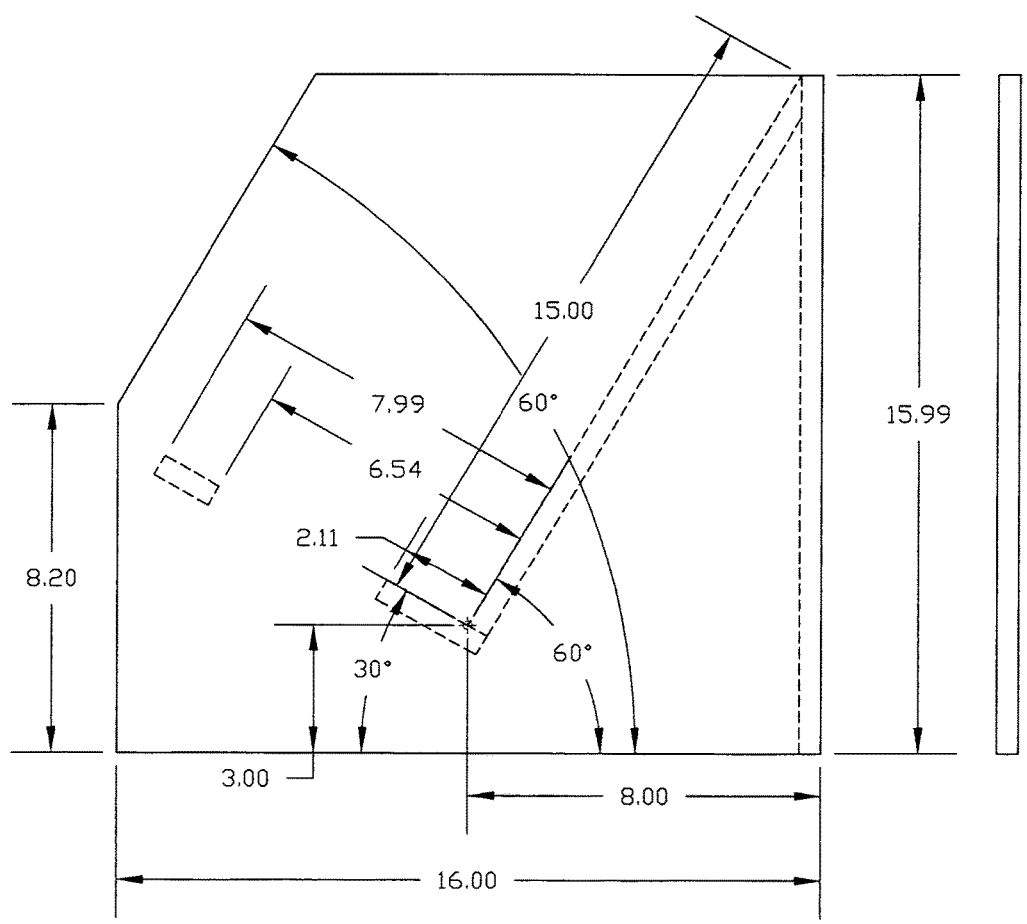
FIG. 21 depicts two views of a side of a stand, i.e., the pivotable, cradling framework, for a grease oxidation device hereof, for example, the Quantum instrument. It is made of "UNOBTANIUM" material and has a #62 surface finish.

Although operating conditions of the ASTM D942 Test Method are beneficially employed, other conditions may be employed such as differing pressures, temperatures, or times. Also, a gas or gas-mixture may be supplied for operations in addition to or in lieu of oxygen or air to, or gas may be evacuated from, the instrument while it is supplied with at least one dish having a grease sample. The gas or gas-mixture may be substantially inert to or reactive with the grease sample, which, of course would include one or more component(s) making up the grease sample.

CONCLUSION TO THE INVENTION

The present invention is thus provided. Various feature(s), part(s), step(s), subcombination(s) and/or combination(s) can be employed with or without reference to other feature(s), part(s), step(s), subcombination(s) and/or combination(s) in the practice of the invention, and numerous and sundry adaptations can be effected within its spirit, the literal claim scope of which is particularly pointed out by the following claims:

What is claimed is:

1. Apparatus comprising a pivotable, cradling framework as a first unit that can hold a rotatable bomb instrument as a second unit distinct and separable from and operable away from the pivotable, cradling framework, wherein the pivotable, cradling framework includes at least one pivot member through which there passes a horizontal axis about which the pivotable, cradling framework can Divot such that, when the pivotable, cradling framework holds the rotatable bomb instrument, the rotatable bomb instrument can be pivoted about the horizontal axis from pivoting the pivotable, cradling framework about the horizontal axis.

2. The apparatus of claim 1, wherein the rotatable bomb instrument includes a bottom and a cylindrical chamber about a chamber axis that is set at an acute angle with respect to the bottom; and, when the pivotable, cradling framework holds the rotatable bomb instrument, the pivotable, cradling framework permits the cylindrical chamber of the rotatable bomb instrument to be tipped to a vertical position with respect to the chamber axis thereof.

3. The apparatus of claim 2, wherein the pivotable, cradling framework includes a stationary member and a pivoting instrument support, which are connectable to one another by, and are pivotable with respect to one another through, the at least one pivot member.

4. The apparatus of claim 3, wherein the stationary member includes at least one stationary side support extending to the at least one pivot member; and the pivoting instrument support includes at least one pivotable side support extending to the at least one pivot member, and at least one of a bottom support and a rear support connectable to the at least one pivotable side support.

5. The pivoting, cradling framework of claim 3, wherein a hollow, annular type, cylindrical insert is inserted in the cylindrical chamber of the rotatable bomb instrument, and a grease rack holding a plurality of dishes as at least one dish for containing a grease sample, in a vertically stacked configuration, is inserted in the hollow portion of the hollow, annular type, cylindrical insert.

6. The apparatus of claim 1, wherein the pivotable, cradling framework includes a stationary member and a pivotable instrument support, wherein:
the at least one member includes a first pivot and a second pivot member;
the stationary member includes a pair of opposing stationary side supports, with a first of the pair of opposing stationary side supports extending to the first pivot member and a second of the pair of opposing stationary side supports extending to the second pivot member; and a connecting member that connects the pair of opposing stationary side supports;
the pivoting instrument support includes a pair of opposing pivotable side supports, with a first of the pair of opposing pivotable side supports extending to the first pivot member and a second of the pair of opposing pivotable side supports extending to the second pivot member; and a bottom support and a rear support connectable to the at least one pivotable side support; and
the first and second pivot members render the stationary member and the pivoting instrument support connectable to one another thereby and pivotable about the horizontal axis with respect to one another therethrough such that the cradling framework that can hold the rotatable bomb instrument is pivotable about the horizontal axis.

7. The apparatus of claim 1, wherein the rotatable bomb instrument is present, and the pivotable, cradling framework holds the rotatable bomb instrument in combination therewith.

8. The apparatus of claim 2, wherein the rotatable bomb instrument is present, and the pivotable, cradling framework holds the rotatable bomb instrument in combination therewith.

9. The apparatus of claim 3, wherein the rotatable bomb instrument is present, and the pivotable, cradling framework holds the rotatable bomb instrument in combination therewith.

10. The apparatus of claim 4, wherein the rotatable bomb instrument is present, and the pivotable, cradling framework holds the rotatable bomb instrument in combination therewith.

11. The apparatus of claim 5, wherein the rotatable bomb instrument is present, and the pivotable, cradling framework holds the rotatable bomb instrument in combination therewith.

12. The apparatus of claim 6, wherein the rotatable bomb instrument is present, and the pivotable, cradling framework holds the rotatable bomb instrument in combination therewith.

13. The apparatus of claim 7, which is useful in measurement of grease oxidation.

14. The apparatus of claim 8, which is useful in measurement of grease oxidation.

15. The apparatus of claim 9, which is useful in measurement of grease oxidation.

16. The apparatus of claim 10, which is useful in measurement of grease oxidation.

17. The apparatus of claim 11, which is useful in measurement of grease oxidation.

18. The apparatus of claim 12, which is useful in measurement of grease oxidation.

19. In combination, apparatus comprising a bomb instrument having a bottom and a hollow reaction chamber having an interior that can hold gas under pressure in the hollow reaction chamber interior, to which is are added to the interior of the hollow reaction chamber, an annular type, cylindrical insert having a hollow interior, and a grease rack.

20. The combination of claim 19, wherein the bomb instrument is bath-free rotatable; the interior of the hollow reaction chamber of the bomb instrument has a cylindrical configuration; the annular type, cylindrical insert having the hollow interior is inserted in the cylindrical interior of the hollow reaction chamber; and the grease rack holds a plurality of dishes as at least one dish for containing a grease sample, in a vertically stacked configuration, and is placed in the hollow interior of the annular type, cylindrical insert, with the cylindrically configured, hollow reaction chamber of the bomb instrument oriented vertically.

* * * * *